US012780822B2

(12) United States Patent
Gong et al.

(10) Patent No.: US 12,780,822 B2
(45) Date of Patent: Nov. 3, 2026

(54) CRYSTALLINE FORM OF NITROGEN-CONTAINING HETEROCYCLIC COMPOUND, PREPARATION METHOD THEREFOR AND USE THEREOF

(71) Applicant: SHANGHAI PHARMACEUTICALS HOLDING CO., LTD., Shanghai (CN)

(72) Inventors: Wanchun Gong, Shanghai (CN); Di Li, Shanghai (CN); Ruipeng Li, Shanghai (CN); Lingjun Duan, Shanghai (CN); Guangxin Xia, Shanghai (CN); Ying Ke, Shanghai (CN)

(73) Assignee: SHANGHAI PHARMACEUTICALS HOLDING CO., LTD., Shanghai (CN)

( * ) Notice: Subject to any disclaimer, the term of this patent is extended or adjusted under 35 U.S.C. 154(b) by 243 days.

(21) Appl. No.: 18/839,040

(22) PCT Filed: Feb. 17, 2023

(86) PCT No.: PCT/CN2023/076920
§ 371 (c)(1),
(2) Date: Aug. 16, 2024

(87) PCT Pub. No.: WO2023/155899
PCT Pub. Date: Aug. 24, 2023

(65) Prior Publication Data

US 2025/0163053 A1 May 22, 2025

(30) Foreign Application Priority Data

Feb. 17, 2022 (CN) ......................... 202210147592.4

(51) Int. Cl.
*C07D 471/04* (2006.01)
*A61K 31/517* (2006.01)
*A61P 35/00* (2006.01)

(52) U.S. Cl.
CPC .......... *C07D 471/04* (2013.01); *A61K 31/517* (2013.01); *A61P 35/00* (2018.01)

(58) Field of Classification Search
CPC ............................ C07D 471/04; A61K 31/517
See application file for complete search history.

(56) References Cited

U.S. PATENT DOCUMENTS

2020/0190091 A1 6/2020 Xia et al.
2024/0197737 A1 6/2024 Li et al.

FOREIGN PATENT DOCUMENTS

WO 2019042409 A1 3/2019
WO 2022206929 A1 10/2022

OTHER PUBLICATIONS

May 19, 2023 International Search Report issued in International Patent Application No. PCT/CN2023/076920.
May 19, 2023 Written Opinion of the International Searching Authority issued in International Patent Application No. PCT/CN2023/076920.

*Primary Examiner* — Valerie Rodriguez-Garcia
*Assistant Examiner* — Karen Cheng

(57) ABSTRACT

Disclosed are a crystalline form of a nitrogen-containing heterocyclic compound, a preparation method therefor and use thereof. The present invention provides crystalline form C of compound 1, and a preparation method therefor, a composition thereof and use thereof in the preparation of medicaments are disclosed. The crystalline form is good in stability and high in bioavailability.

1

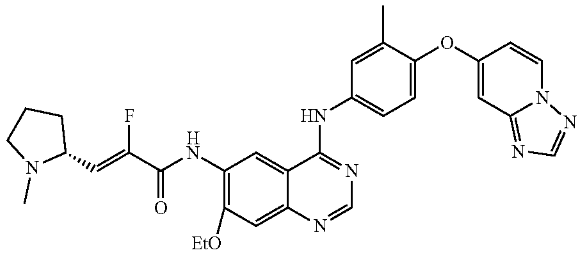

19 Claims, 14 Drawing Sheets

CRYSTALLINE FORM OF NITROGEN-CONTAINING HETEROCYCLIC COMPOUND, PREPARATION METHOD THEREFOR AND USE THEREOF

The present application is a National Stage of International Application No. PCT/CN2023/076920, filed on Feb. 17, 2023, which claims the right of the priority of Chinese patent application No. 2022101475924 filed on Feb. 17, 2022. The contents of the above Chinese patent application are incorporated herein by reference in its entirety.

TECHNICAL FIELD

The present disclosure relates to a nitrogen-containing heterocyclic compound, a preparation method therefor, and a use thereof.

BACKGROUND

A nitrogen-containing heterocyclic compound, designated as compound 1, having the chemical name (R,Z)—N-(4-((4-([1,2,4]triazolo[1,5-a]pyridin-7-yloxy)-3-methylphenyl)amino)-7-ethoxyquinazolin-6-yl)-2-fluoro-3-(1-methylpyrrolidin-2-yl)acrylamide, with a molecular formula of $C_{31}H_{31}FN_8O_3$, and having the structural formula shown below:

1

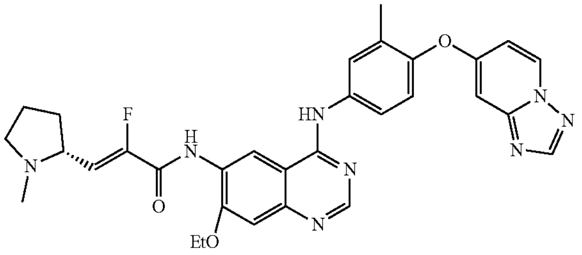

CN109422755 and WO2019042409 disclose this nitrogen-containing heterocyclic compound and its preparation method. The compound 1 obtained by the method disclosed in the patent is a yellow, foamy solid with undesirable solid-state properties. It also shows that compound 1 is a small molecule inhibitor that either weakens the EGFR kinase inhibitory activity or is selective for the ErbB2 target.

CONTENT OF THE PRESENT INVENTION

The technical problem to be solved by the present disclosure is to overcome the defects in the prior art of the undesirable solid-state properties of (R,Z)—N-(4-((4-([1,2,4]triazolo[1,5-a]pyridin-7-yloxy)-3-methylphenyl)amino)-7-ethoxyquinazolin-6-yl)-2-fluoro-3-(1-methylpyrrolidin-2-yl)acrylamide, and to provide a crystal form of this compound, a preparation method therefor, and a use thereof, wherein the crystal form exhibits high stability and good bioavailability.

The present disclosure solves the aforementioned technical problem through the following technical solutions:

The present disclosure provides a crystal form C of compound 1;

1

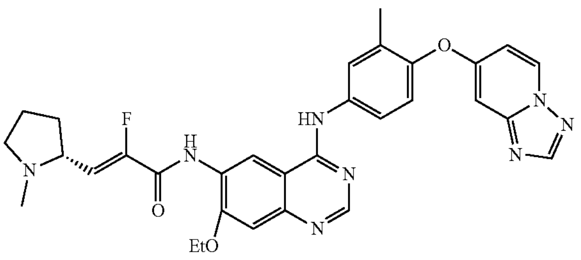

the crystal form C has an X-ray powder diffraction pattern expressed in 2θ angles comprising diffraction peaks at positions as follows: 5.32±0.2°, 8.42±0.2°, 10.62±0.2°, 11.48±0.2°, 13.46±0.2°, 16.14±0.2°, 16.57±0.2°, 16.96±0.2°, 17.26±0.2°, and 18.11±0.2° using Cu-Kα radiation.

In a certain embodiment, the X-ray powder diffraction pattern of the crystal form C expressed in 2θ angles further comprises diffraction peaks at one or more positions as follows: 19.42±0.2°, 21.26±0.2°, 22.11±0.2°, 22.73±0.2°, 23.05±0.2°, 23.45±0.2°, 25.98±0.2°, 26.71±0.2°, and 26.89±0.2°; the X-ray powder diffraction pattern of the crystal form C expressed in 2θ angles preferably further comprises diffraction peaks at one or more positions as follows: 12.23±0.2°, 13.00±0.2°, 14.76±0.2°, 20.33±0.2°, 24.89±0.2°, 28.50±0.2°, 31.74±0.2°, 34.46±0.2°, 35.94±0.2°, and 37.67±0.2°.

In a certain embodiment, the X-ray powder diffraction pattern of the crystal form C expressed in 2θ angles comprises diffraction peaks as shown in the table below:

| Diffraction angle (°2θ) | d-Spacing (Å) | Relative intensity (%) |
|---|---|---|
| 5.32 | 16.62 | 74.21 |
| 8.42 | 10.51 | 16.85 |
| 10.62 | 8.33 | 33.15 |
| 11.48 | 7.71 | 76.93 |
| 12.23 | 7.24 | 7.17 |
| 13.00 | 6.81 | 8.22 |
| 13.46 | 6.58 | 26.98 |
| 14.76 | 6.00 | 8.36 |
| 16.14 | 5.49 | 28.59 |
| 16.57 | 5.35 | 78.16 |
| 16.96 | 5.23 | 58.96 |
| 17.26 | 5.14 | 55.51 |
| 18.11 | 4.90 | 100.00 |
| 19.42 | 4.57 | 24.10 |
| 20.33 | 4.37 | 10.44 |
| 21.26 | 4.18 | 65.07 |
| 22.11 | 4.02 | 44.06 |
| 22.73 | 3.91 | 22.24 |
| 23.05 | 3.86 | 68.68 |
| 23.45 | 3.79 | 26.23 |
| 24.89 | 3.58 | 10.74 |
| 25.98 | 3.43 | 23.94 |
| 26.71 | 3.34 | 38.70 |
| 26.89 | 3.32 | 55.25 |
| 28.50 | 3.13 | 18.99 |
| 31.74 | 2.82 | 7.39 |
| 34.46 | 2.60 | 1.90 |
| 35.94 | 2.50 | 1.47 |
| 37.67 | 2.39 | 3.97. |

In a certain embodiment, the X-ray powder diffraction pattern of the crystal form C expressed in 2θ angles is basically as shown in FIG. 5.

In a certain embodiment, the crystal form C has a differential scanning calorimetry pattern comprising an endothermic peak at 213.3° C. (onset temperature).

In a certain embodiment, the differential scanning calorimetry pattern of the crystal form C comprises an endothermic peak at 213.3° C. (onset temperature), with a heat of fusion of 95.16 J/g.

In a certain embodiment, the differential scanning calorimetry pattern of the crystal form C is basically as shown in FIG. 6.

In a certain embodiment, the crystal form C has a thermogravimetric analysis pattern showing a weight loss of 2.1% when heated to 200° C. and an additional weight loss of 1.5% when further heated to 230° C.

In a certain embodiment, the thermogravimetric analysis pattern of the crystal form C is basically as shown in FIG. 6.

The present disclosure further provides a preparation method for the crystal form C, which follows scheme 1 or scheme 2;

the scheme 1 comprises the following step: obtaining the crystal form C of the compound 1 by performing a crystal transformation on a suspension of compound 1 in a solvent;

1

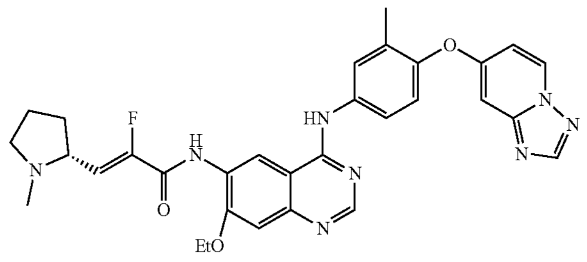

the compound 1 exists in one of crystal forms B, A, G, H, I, M, and E; the crystal form B has an X-ray powder diffraction pattern expressed in 2θ angles comprising diffraction peaks at positions as follows: 7.53±0.2°, 8.83±0.2°, 12.72±0.2°, 13.98±0.2°, 14.20±0.2°, 15.05±0.2°, 15.44±0.2°, 17.68±0.2°, 18.13±0.2°, 18.38±0.2°, 18.86±0.2°, 21.24±0.2°, 22.44±0.2°, and 24.54±0.2° using Cu-Kα radiation; the crystal form A has an X-ray powder diffraction pattern expressed in 2θ angles comprising diffraction peaks at positions as follows: 5.97±0.2°, 12.27±0.2°, 13.30±0.2°, 14.31±0.2°, 16.08±0.2°, 16.60±0.2°, 17.93±0.2°, and 20.24±0.2° using Cu-Kα radiation; the crystal form G has an X-ray powder diffraction pattern expressed in 2θ angles comprising diffraction peaks at positions as follows: 6.41±0.2°, 6.88±0.2°, 8.75±0.2°, 12.82±0.2°, 13.38±0.2°, 13.73±0.2°, 16.74±0.2°, 17.64±0.2°, 19.24±0.2°, 21.68±0.2°, 22.77±0.2°, 26.14±0.2°, and 26.49±0.2° using Cu-Kα radiation; the crystal form H has an X-ray powder diffraction pattern expressed in 2θ angles comprising diffraction peaks at positions as follows: 5.41±0.2°, 6.13±0.2°, 7.92±0.2°, 11.19±0.2°, 12.26±0.2°, and 21.91±0.2° using Cu-Kα radiation; the crystal form I has an X-ray powder diffraction pattern expressed in 2θ angles comprising diffraction peaks at positions as follows: 6.80±0.2°, 7.22±0.2°, 8.03±0.2°, 8.35±0.2°, 9.70±0.2°, 10.28±0.2°, and 19.84±0.2° using Cu-Kα radiation; the crystal form M has an X-ray powder diffraction pattern expressed in 2θ angles comprising diffraction peaks at positions as follows: 5.52±0.2°, 7.96±0.2°, 9.41±0.2°, 13.36±0.2°, 14.68±0.2°, 17.93±0.2°, 18.70±0.2°, 25.75±0.2°, 26.11±0.2°, and 26.50±0.2° using Cu-Kα radiation; the crystal form E has an X-ray powder diffraction pattern expressed in 2θ angles comprising diffraction peaks at positions as follows: 6.07±0.2°, 8.97±0.2°, 9.32±0.2°, 9.87±0.2°, 13.05±0.2°, 13.27±0.2°, 14.09±0.2°, 15.78±0.2°, 16.98±0.2°, 18.27±0.2°, 18.47±0.2°, 21.26±0.2°, and 22.41±0.2° using Cu-Kα radiation;

when the compound 1 exists in one of crystal forms A, G, H, I, M, and E, the solvent is acetone or acetone/water;

when the compound 1 exists in crystal form B, the solvent is acetonitrile or ethanol;

the scheme 2 comprises the following step: obtaining the crystal form C of the compound 1 by performing a crystallization on compound 1 in a solvent; the solvent is an alcohol solvent, preferably ethanol or isopropanol.

In the preparation method for the crystal form C, when the scheme 1 is adopted and the solvent is acetone/water, the volume ratio of acetone to water is between 986:14 and 950:50.

In the preparation method for the crystal form C, when the scheme 1 is adopted and the compound 1 exists in one of crystal forms A, G, H, I, M, and E, the crystal transformation is performed at a temperature of 20° C. to 30° C. (room temperature).

In the preparation method for the crystal form C, when the scheme 1 is adopted and the compound 1 exists in crystal form B, the crystal transformation is performed at a temperature of 20° C. to 50° C., such as 20° C. to 30° C. (room temperature).

In the preparation method for the crystal form C, when the scheme 2 is adopted, the mass-to-volume ratio of the compound 1 to the solvent is 100 mg:2 mL.

In the preparation method for the crystal form C, when the scheme 2 is adopted, the crystallization is performed at a temperature of 50° C. to 60° C., preferably 55° C.

In the preparation method for the crystal form C, when the scheme 2 is adopted, the crystallization is performed for a duration of 24 hours.

The present disclosure further provides a pharmaceutical composition comprising the aforementioned crystal form C and a pharmaceutical excipient.

The present disclosure further provides a use of the aforementioned crystal form C in the preparation of a medicament, and the medicament may be used for treating cancer and/or diseases treated by inhibiting EGFR and/or ErbB2 receptor tyrosine kinases, such as diseases treated by selectively inhibiting the ErbB2 receptor tyrosine kinase; the cancer and diseases may be breast cancer, gastric cancer, ovarian cancer, lung cancer, etc.; the crystal form C may be used in a therapeutically effective amount.

The present disclosure further provides a use of the aforementioned crystal form C in the preparation of an EGFR and/or ErbB2 receptor tyrosine kinase inhibitor. The EGFR and/or ErbB2 receptor tyrosine kinase inhibitor may be a selective ErbB2 receptor tyrosine kinase inhibitor.

In the present disclosure, "room temperature" refers to 20° C. to 30° C.

Without departing from the common knowledge in the art, the above various preferred conditions can be arbitrarily combined to obtain the various preferred embodiments of the present disclosure.

The reagents and raw materials used in the present disclosure are commercially available.

The positive and progressive effect of the present disclosure lies in overcoming the shortcomings of the undesirable solid-state properties of (R,Z)—N-(4-((4-([1,2,4]triazolo[1, 5-a]pyridin-7-yloxy)-3-methylphenyl)amino)-7-ethoxyquinazolin-6-yl)-2-fluoro-3-(1-methylpyrrolidin-2-yl)acrylamide in the prior art, by providing a crystal form of the compound with high stability and good bioavailability.

DETAILED DESCRIPTION OF THE PREFERRED EMBODIMENT

Figure 1:
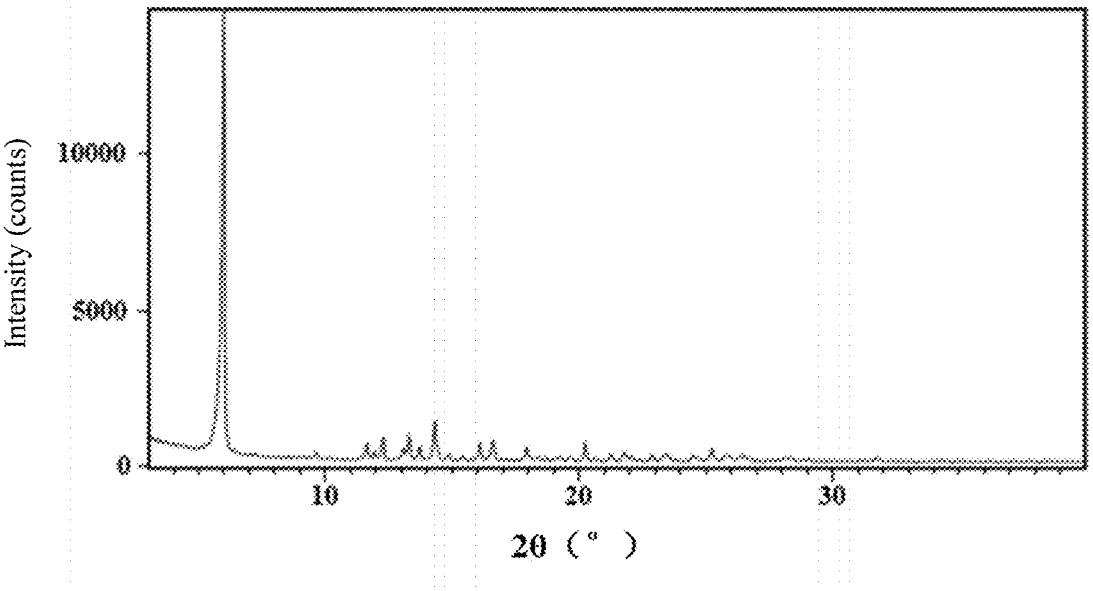
FIG. 1: XRPD pattern of crystal form A.

The present disclosure is further described through examples below, but is not limited to the scope of the examples provided.

The abbreviations used in the present disclosure are explained as follows:

XRPD—X-ray Powder Diffraction
TGA—Thermogravimetric Analysis
DSC—Differential Scanning Calorimetry
DVS—Dynamic Vapor Sorption The testing conditions are as follows:

XRPD

The X-ray powder diffraction patterns described in the present disclosure were collected using the PANalytical Empyrean X-ray powder diffractometer and the PANalytical X'Pert$^3$ X-ray powder diffractometer.

Method parameters for the Empyrean X-ray powder diffractometer are as follows:

X-ray type: Cu, Kα
Kα1 (Å): 1.540598; Kα2 (Å): 1.544426
Kα2/Kα1 intensity ratio: 0.50
Voltage: 45 kV
Current: 40 mA
Divergence slit: Automatic
Scanning mode: Continuous Scanning range: 3.0 to 40.0 degrees
Scanning time per step: 17.780 seconds
Step size: 0.0167 degrees Method parameters for the PANalytical X'Pert$^3$ X-ray powder diffractometer are as follows:

X-ray type: Cu, Kα
Kα1 (Å): 1.540598; Kα2 (Å): 1.544426
Kα2/Kα1 intensity ratio: 0.50
Voltage: 45 kV
Current: 40 mA
Divergence slit: 1/16 degree
Scanning mode: Continuous
Scanning range: 3.0 to 40.0 degrees
Scanning time per step: 46.665 seconds
Step size: 0.0263 degrees

DSC

The differential scanning calorimetry (DSC) data described in the present disclosure were obtained using the TA Instruments Q200 and TA Instruments Q2000 DSC instruments. The instrument control software used was Q Series, and the analysis software was Universal Analysis. Typically, 1 to 10 milligrams of the sample was placed in a lidded aluminum crucible (unless otherwise specified). The sample was heated from room temperature to 300° C. at a rate of 10° C./min under a dry nitrogen atmosphere with a flow rate of 50 mL/min. The TA software recorded the heat changes of the sample during the heating process. In the present disclosure, the melting point was reported based on the onset temperature.

TGA

The thermogravimetric analysis (TGA) data described in the present disclosure were obtained using the TA Instruments Q500 and TA Instruments Q5000 TGA instruments. The instrument control software used was Q Series, and the analysis software was Universal Analysis. Typically, 2 to 15 mg of the sample was placed in a platinum crucible. Using a segmented high-resolution detection mode, the sample was heated from room temperature to 400° C. at a rate of 10° C./min under a dry nitrogen atmosphere with a flow rate of 50 mL/min. The TA software recorded the weight changes of the sample during the heating process.

DVS

The dynamic vapor sorption patterns described in the present disclosure were collected using the Intrinsic and Intrinsic Plus dynamic vapor sorption analyzers from SMS Company. The method parameters for the dynamic vapor sorption testing in the present disclosure are as follows:

Temperature: 25° C.
Protective gas and flow rate: $N_2$, 200 mL/min
dm/dt: 0.002%/min
Minimum dm/dt equilibrium time: 10 minutes
Maximum equilibrium time: 180 minutes
Relative humidity range: 0% RH to 95% RH to 0% RH
Relative humidity gradient: 10% (0% RH to 90% RH to 0% RH), 5% (90% RH to 95% RH and 95% RH to 90% RH)

Preparation Example of Amorphous Form of Compound 1

Example 1

Figure 26:
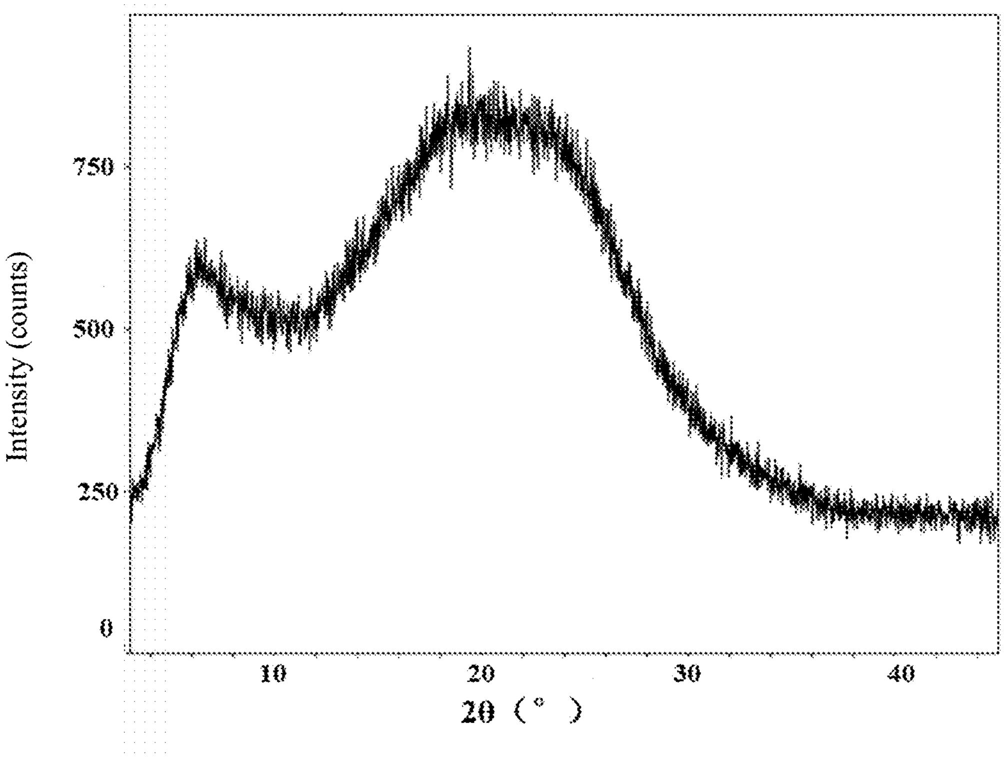
FIG. 26: XRPD pattern of amorphous form.

The structure of compound 1 is as follows, and the amorphous form thereof was prepared according to Example 45 of patents CN109422755 and WO2019042409. This amorphous form is a yellow, foamy solid with undesirable solid-state properties. The XRPD pattern of the amorphous form is shown in FIG. 26.

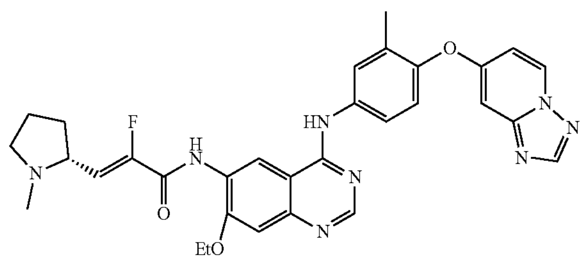

Preparation Example of Crystal Forms

Example 1 (Crystal form A of Compound 1)

Figure 2:
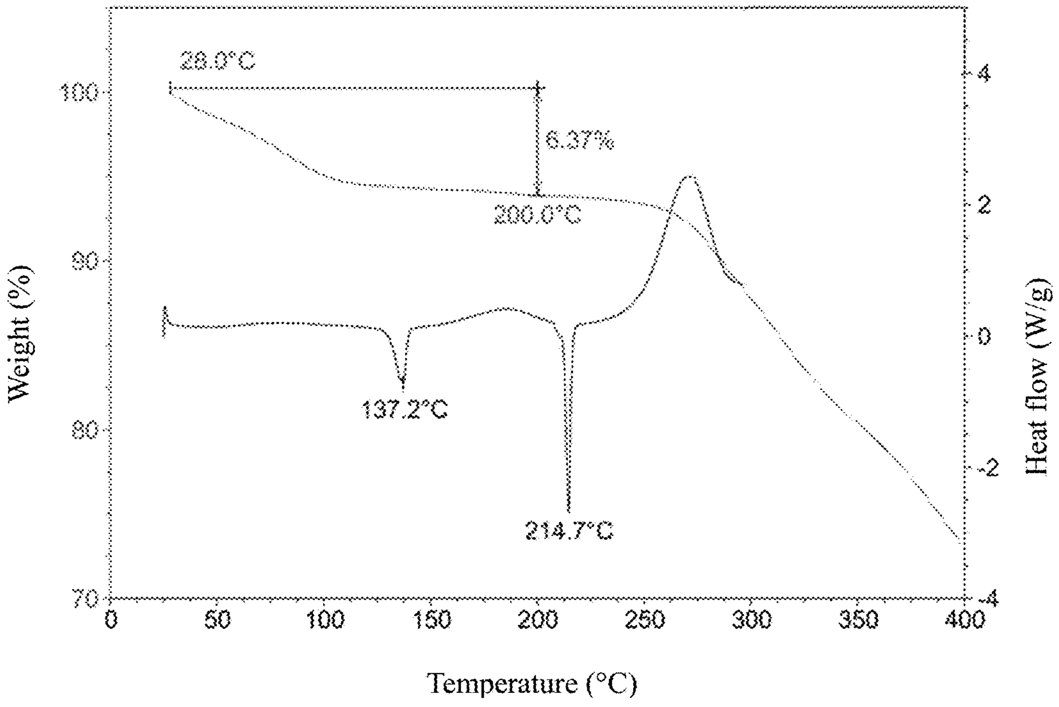
FIG. 2: TGA/DSC pattern of crystal form A.

100 mg of crystal form B of compound 1 was suspended in 1 mL of EtOAc and stirred at room temperature for five days. The XRPD pattern of the resulting solid is shown in FIG. 1. The TGA and DSC patterns are shown in FIG. 2. TGA data indicates that the crystal form sample lost 6.4% of its weight when heated to 200° C., and the DSC shows two endothermic peaks at 137.2° C. and 214.7° C. (peak temperature). The results confirm that the resulting solid product is the crystal form A as described in the present disclosure.

TABLE 1

XRPD data of crystal form A

| Diffraction angle (°2θ) | d-Spacing (Å) | Relative intensity (%) |
|---|---|---|
| 5.97 | 14.80 | 100.00 |
| 9.62 | 9.19 | 1.59 |
| 11.62 | 7.62 | 3.74 |
| 11.92 | 7.42 | 1.65 |
| 12.27 | 7.22 | 4.98 |
| 13.07 | 6.78 | 2.48 |
| 13.30 | 6.66 | 5.55 |
| 13.71 | 6.46 | 3.11 |
| 14.31 | 6.19 | 9.01 |
| 14.88 | 5.95 | 1.18 |
| 15.39 | 5.76 | 0.72 |
| 16.08 | 5.51 | 4.19 |
| 16.60 | 5.34 | 4.21 |
| 17.93 | 4.95 | 3.09 |
| 18.37 | 4.83 | 0.75 |
| 19.22 | 4.62 | 0.71 |
| 19.66 | 4.52 | 0.61 |
| 20.24 | 4.39 | 4.13 |
| 21.28 | 4.17 | 1.40 |
| 21.77 | 4.08 | 1.81 |
| 22.89 | 3.89 | 1.33 |
| 23.47 | 3.79 | 1.38 |
| 24.50 | 3.63 | 1.21 |
| 25.25 | 3.53 | 2.72 |
| 25.79 | 3.45 | 1.26 |
| 26.46 | 3.37 | 1.16 |
| 28.25 | 3.16 | 0.61 |
| 31.75 | 2.82 | 0.71 |

Example 2 (Crystal Form B of Compound 1)

Figure 3:
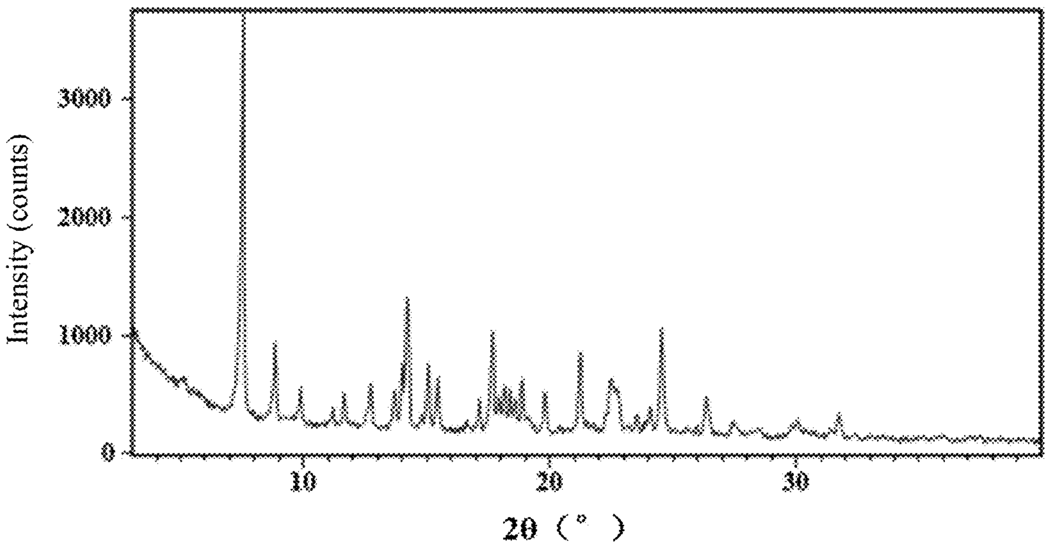
FIG. 3: XRPD pattern of crystal form B.
Figure 4:
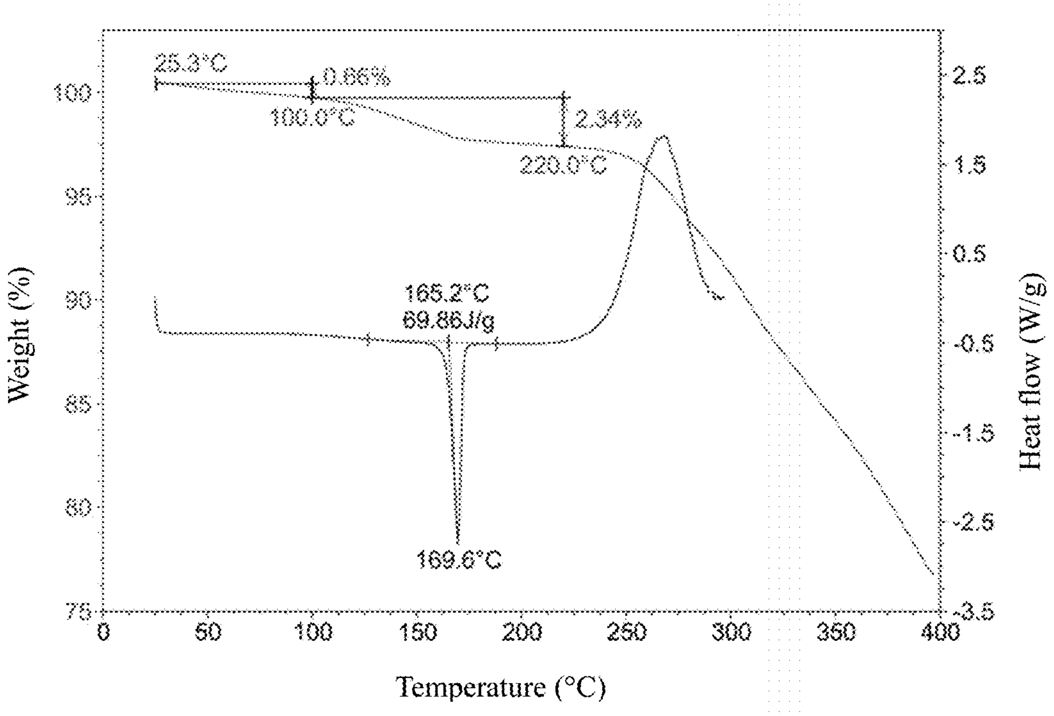
FIG. 4: TGA/DSC pattern of crystal form B.

100 mg of the amorphous form of compound 1 was stirred and crystallized in 1 mL of acetone at room temperature for 2 hours. The X-ray powder diffraction data of the resulting solid are shown in Table 2, and the XRPD pattern thereof is shown in FIG. 3. The TGA/DSC patterns are shown in FIG. 4. The sample lost 0.7% of its weight when heated from room temperature to 100° C., and lost an additional 2.3% of its weight when further heated to 220° C. An endothermic peak was observed at 165.2° C. (onset temperature), which is presumed to be the melting signal of the sample. The results confirm that the resulting solid product is the crystal form B as described in the present disclosure.

TABLE 2

XRPD data of crystal form B

| Diffraction angle (°2θ) | d-Spacing (Å) | Relative intensity (%) |
|---|---|---|
| 7.53 | 11.75 | 100.00 |
| 8.83 | 10.02 | 18.57 |
| 9.86 | 8.97 | 8.55 |
| 11.14 | 7.94 | 2.90 |
| 11.63 | 7.61 | 7.78 |
| 12.72 | 6.96 | 10.12 |
| 13.69 | 6.47 | 7.91 |
| 13.98 | 6.33 | 15.12 |
| 14.20 | 6.24 | 30.79 |
| 15.05 | 5.89 | 15.58 |
| 15.44 | 5.74 | 12.55 |
| 17.13 | 5.18 | 7.48 |
| 17.68 | 5.02 | 23.85 |
| 17.91 | 4.95 | 8.24 |
| 18.13 | 4.89 | 10.52 |
| 18.38 | 4.83 | 10.03 |
| 18.60 | 4.77 | 7.47 |
| 18.86 | 4.70 | 12.63 |
| 19.80 | 4.48 | 9.58 |
| 21.24 | 4.18 | 19.45 |
| 22.44 | 3.96 | 12.75 |
| 22.78 | 3.90 | 9.63 |
| 23.52 | 3.78 | 4.15 |
| 24.07 | 3.70 | 6.64 |
| 24.54 | 3.63 | 25.40 |
| 26.35 | 3.38 | 9.61 |
| 27.44 | 3.25 | 2.89 |
| 29.97 | 2.98 | 2.87 |
| 31.76 | 2.82 | 5.20 |

Example 3 (Crystal Form C of Compound 1)

Figure 5:
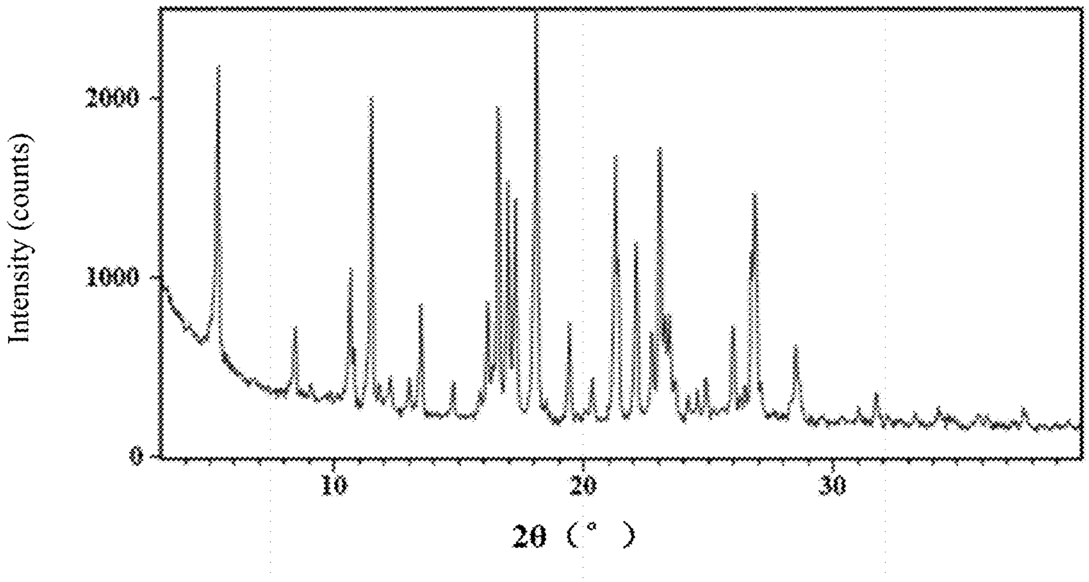
FIG. 5: XRPD pattern of crystal form C.
Figure 6:
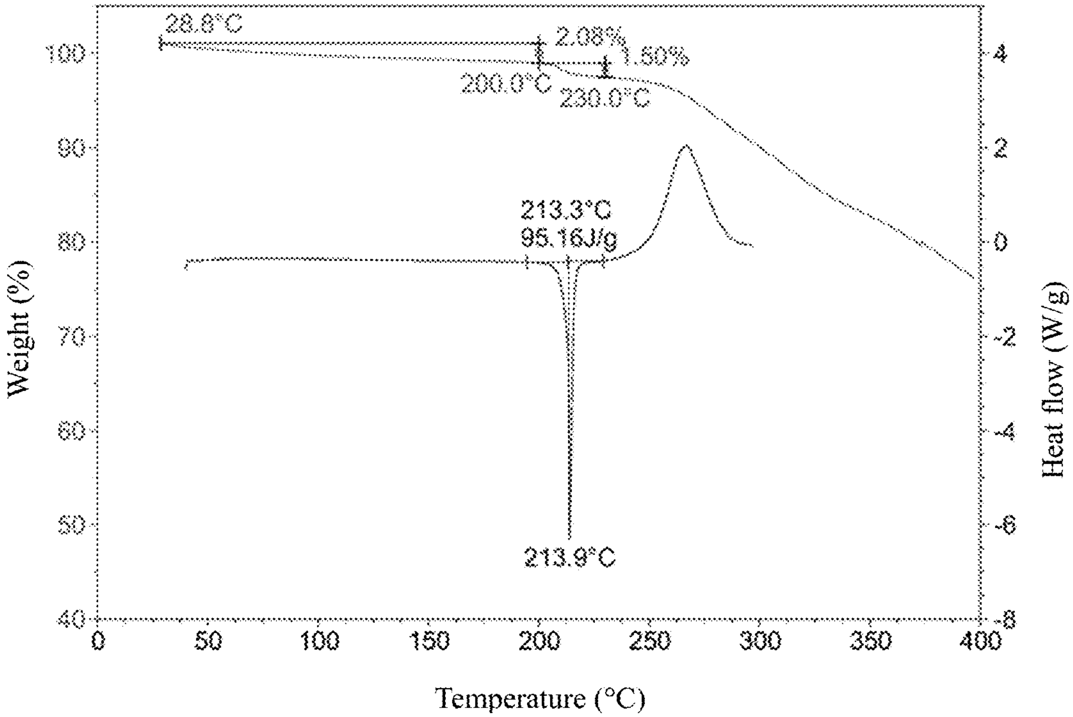
FIG. 6: TGA/DSC pattern of crystal form C.

100 mg of the amorphous form of compound 1 was stirred and crystallized in 2 mL of ethanol at 50-60° C. for 24 hours. The X-ray powder diffraction data of the resulting solid are shown in Table 3, and the XRPD pattern thereof is shown in FIG. 5. The TGA/DSC results are shown in FIG. 6. The sample lost 2.1% of its weight when heated from room temperature to 200° C., and lost an additional 1.5% of its weight when further heated to 230° C. An endothermic peak was observed at 213.3° C. (onset temperature), which is presumed to be the melting signal of the sample, with a heat of fusion of 95.16 J/g. The results confirm that the resulting solid product is the crystal form C as described in the present disclosure.

TABLE 3

XRPD data of crystal form C

| Diffraction angle (°2θ) | d-Spacing (Å) | Relative intensity (%) |
|---|---|---|
| 5.32 | 16.62 | 74.21 |
| 8.42 | 10.51 | 16.85 |
| 10.62 | 8.33 | 33.15 |
| 11.48 | 7.71 | 76.93 |
| 12.23 | 7.24 | 7.17 |
| 13.00 | 6.81 | 8.22 |
| 13.46 | 6.58 | 26.98 |
| 14.76 | 6.00 | 8.36 |
| 16.14 | 5.49 | 28.59 |

TABLE 3-continued

| XRPD data of crystal form C | | |
|---|---|---|
| Diffraction angle (°2θ) | d-Spacing (Å) | Relative intensity (%) |
| 16.57 | 5.35 | 78.16 |
| 16.96 | 5.23 | 58.96 |
| 17.26 | 5.14 | 55.51 |
| 18.11 | 4.90 | 100.00 |
| 19.42 | 4.57 | 24.10 |
| 20.33 | 4.37 | 10.44 |
| 21.26 | 4.18 | 65.07 |
| 22.11 | 4.02 | 44.06 |
| 22.73 | 3.91 | 22.24 |
| 23.05 | 3.86 | 68.68 |
| 23.45 | 3.79 | 26.23 |
| 24.89 | 3.58 | 10.74 |
| 25.98 | 3.43 | 23.94 |
| 26.71 | 3.34 | 38.70 |
| 26.89 | 3.32 | 55.25 |
| 28.50 | 3.13 | 18.99 |
| 31.74 | 2.82 | 7.39 |
| 34.46 | 2.60 | 1.90 |
| 35.94 | 2.50 | 1.47 |
| 37.67 | 2.39 | 3.97 |

Example 4 (Crystal Form D)

Figure 7:
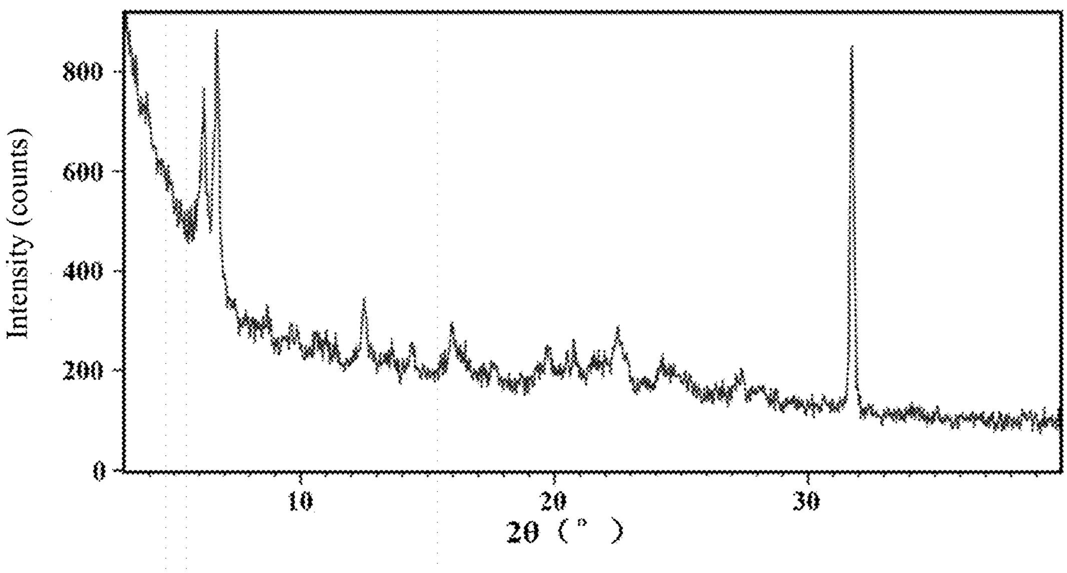
FIG. 7: XRPD pattern of crystal form D.

5 mg of the amorphous form of compound 1 was stirred and crystallized in 1 mL of 2-methyltetrahydrofuran (2-MeTHF) at 50° C. for four days. The X-ray powder diffraction data of the resulting solid are shown in Table 4, and the XRPD pattern thereof is shown in FIG. 7. The results confirm that the resulting solid product is the crystal form D as described in the present disclosure.

TABLE 4

| XRPD data of crystal form D | | |
|---|---|---|
| Diffraction angle (°2θ) | d-Spacing (Å) | Relative intensity (%) |
| 6.19 | 14.29 | 41.01 |
| 6.70 | 13.20 | 65.66 |
| 12.49 | 7.09 | 16.21 |
| 16.07 | 5.51 | 8.52 |
| 22.50 | 3.95 | 12.39 |
| 31.72 | 2.82 | 100.00 |

Example 5 (Crystal Form E)

Figure 8:
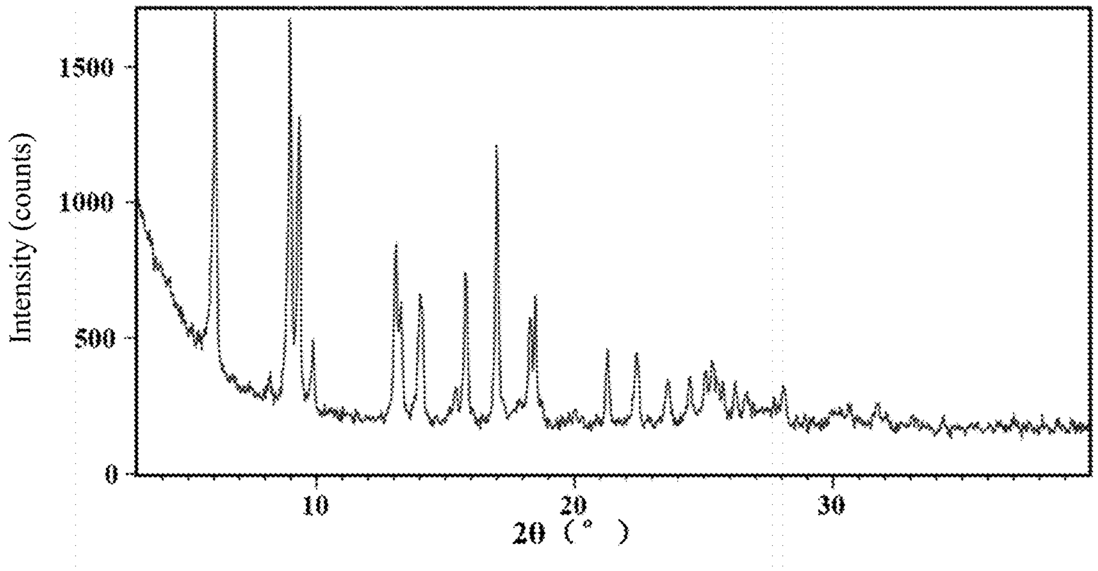
FIG. 8: XRPD pattern of crystal form E.
Figure 9:
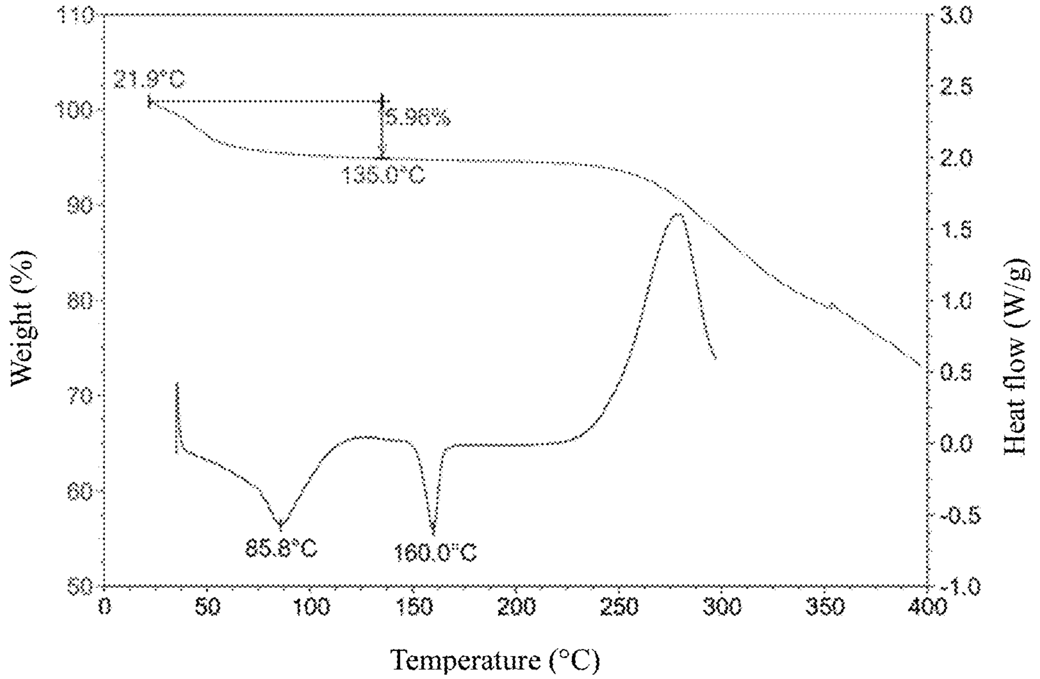
FIG. 9: TGA/DSC pattern of crystal form E.

100 mg of crystal form B of compound 1 was suspended and stirred in 1 mL of Acetone/$H_2O$ (605:395, v/v) at room temperature for three days. The X-ray powder diffraction data of the solid obtained from repeated preparation are shown in Table 5, and the XRPD pattern thereof is shown in FIG. 8. The TGA/DSC results are shown in FIG. 9. The sample lost 6.0% of its weight when heated from room temperature to 135° C., and two endothermic peaks were observed at 85.8° C. (peak temperature) and 160.0° C. (peak temperature). The results confirm that the resulting solid product is the crystal form E as described in the present disclosure.

TABLE 5

| XRPD data of crystal form E | | |
|---|---|---|
| Diffraction angle (°2θ) | d-Spacing (Å) | Relative intensity (%) |
| 6.07 | 14.57 | 91.77 |
| 8.97 | 9.85 | 100.00 |
| 9.32 | 9.49 | 76.64 |
| 9.87 | 8.96 | 18.12 |
| 13.05 | 6.78 | 44.04 |
| 13.27 | 6.67 | 31.10 |
| 14.09 | 6.28 | 29.37 |
| 15.78 | 5.62 | 38.84 |
| 16.98 | 5.22 | 72.71 |
| 18.27 | 4.86 | 27.83 |
| 18.47 | 4.80 | 33.43 |
| 21.26 | 4.18 | 19.00 |
| 22.41 | 3.97 | 18.53 |
| 23.60 | 3.77 | 11.44 |
| 24.45 | 3.64 | 11.92 |
| 25.20 | 3.53 | 11.11 |
| 26.22 | 3.40 | 10.95 |
| 28.10 | 3.18 | 10.27 |
| 30.28 | 2.95 | 3.01 |
| 31.70 | 2.82 | 4.98 |

Example 6 (Crystal Form F)

Figure 10:
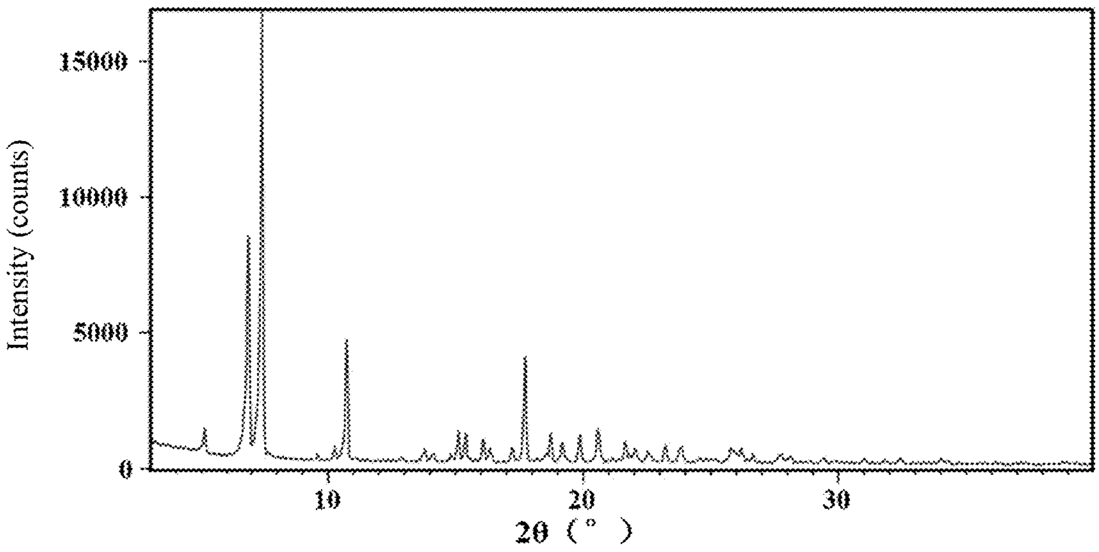
FIG. 10: XRPD pattern of crystal form F.
Figure 11:
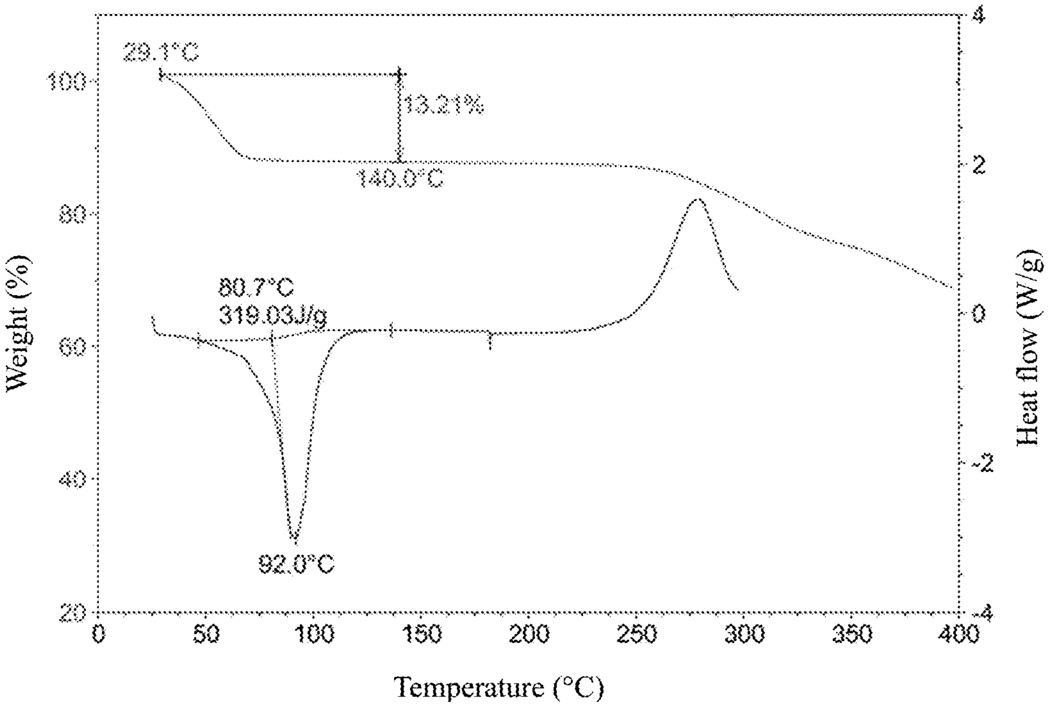
FIG. 11: TGA/DSC pattern of crystal form F.

2 mg of crystal form B of compound 1 was suspended and stirred in 1 mL of Acetone/$H_2O$ (605:395, v/v) at room temperature for one day. The X-ray powder diffraction data of the resulting solid are shown in Table 6, and the XRPD pattern thereof is shown in FIG. 10. The TGA/DSC results are shown in FIG. 11. The sample lost 13.2% of its weight when heated from room temperature to 140° C., and an endothermic peak was observed at 80.7° C. (onset temperature). The results confirm that the resulting solid product is the crystal form F as described in the present disclosure.

TABLE 6

| XRPD data of crystal form F | | |
|---|---|---|
| Diffraction angle (°2θ) | d-Spacing (Å) | Relative intensity (%) |
| 5.14 | 17.21 | 5.18 |
| 6.85 | 12.90 | 50.75 |
| 7.40 | 11.95 | 100.00 |
| 9.57 | 9.24 | 1.25 |
| 10.24 | 8.64 | 2.99 |
| 10.72 | 8.25 | 27.12 |
| 12.87 | 6.88 | 0.66 |
| 13.78 | 6.43 | 2.53 |
| 14.07 | 6.30 | 1.80 |
| 15.10 | 5.87 | 6.92 |
| 15.37 | 5.76 | 6.08 |
| 16.08 | 5.51 | 5.04 |
| 16.33 | 5.43 | 3.05 |
| 17.22 | 5.15 | 3.20 |
| 17.71 | 5.01 | 23.26 |
| 18.73 | 4.74 | 6.18 |
| 19.17 | 4.63 | 4.17 |
| 19.87 | 4.47 | 5.98 |
| 20.57 | 4.32 | 7.39 |
| 21.65 | 4.10 | 4.37 |
| 22.03 | 4.03 | 3.00 |
| 22.51 | 3.95 | 2.53 |
| 23.22 | 3.83 | 3.91 |
| 23.86 | 3.73 | 3.35 |
| 25.77 | 3.46 | 3.34 |
| 26.20 | 3.40 | 3.08 |
| 26.66 | 3.34 | 1.78 |
| 27.78 | 3.21 | 1.93 |
| 28.13 | 3.17 | 1.41 |
| 29.39 | 3.04 | 1.01 |

TABLE 6-continued

| XRPD data of crystal form F | | |
|---|---|---|
| Diffraction angle (°2θ) | d-Spacing (Å) | Relative intensity (%) |
| 29.89 | 2.99 | 0.52 |
| 31.00 | 2.89 | 1.02 |
| 31.85 | 2.81 | 0.50 |
| 32.44 | 2.76 | 1.19 |
| 34.01 | 2.64 | 1.16 |

Example 7 (Crystal Form G)

Figure 12:
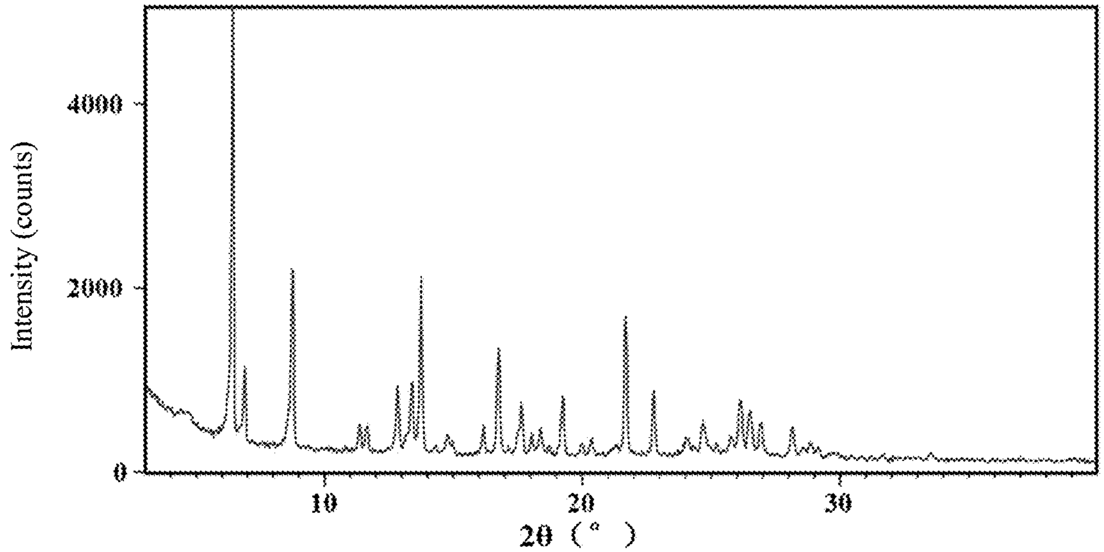
FIG. 12: XRPD pattern of crystal form G.
Figure 13:
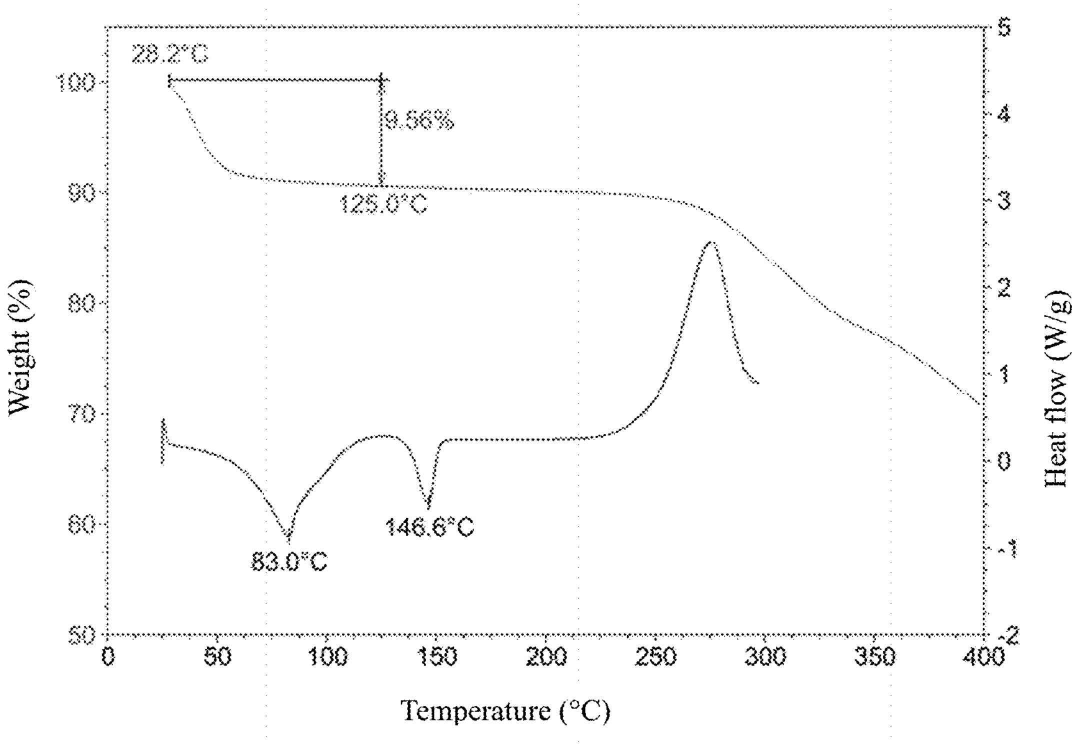
FIG. 13: TGA/DSC pattern of crystal form G.

100 mg of crystal form B of compound 1 was weighed and dissolved in 21 mL of $CHCl_3$/MeOH (1:20, v/v). The sample was filtered, then sealed with a sealing film, with several small holes punctured in the sealing film, and left to evaporate naturally at room temperature in a fume hood. The X-ray powder diffraction data of the resulting solid are shown in Table 7, and the XRPD pattern thereof is shown in FIG. 12. The TGA/DSC results are shown in FIG. 13. The sample lost 9.6% of its weight when heated from room temperature to 125° C., and two endothermic peaks were observed at 83.0° C. and 146.6° C. (peak temperature). The results confirm that the resulting solid product is the crystal form G as described in the present disclosure.

TABLE 7

| XRPD data of crystal form G | | |
|---|---|---|
| Diffraction angle (°2θ) | d-Spacing (Å) | Relative intensity (%) |
| 4.60 | 19.19 | 1.47 |
| 6.41 | 13.78 | 100.00 |
| 6.88 | 12.85 | 17.19 |
| 8.75 | 10.11 | 41.66 |
| 11.35 | 7.79 | 5.99 |
| 11.63 | 7.61 | 5.57 |
| 12.82 | 6.90 | 15.52 |
| 13.38 | 6.62 | 16.07 |
| 13.73 | 6.45 | 40.78 |
| 14.76 | 6.00 | 4.37 |
| 16.16 | 5.49 | 6.79 |
| 16.74 | 5.29 | 24.19 |
| 17.64 | 5.03 | 11.28 |
| 18.02 | 4.92 | 4.99 |
| 18.37 | 4.83 | 5.97 |
| 19.24 | 4.61 | 13.57 |
| 19.98 | 4.44 | 2.61 |
| 20.35 | 4.36 | 3.89 |
| 21.68 | 4.10 | 31.99 |
| 22.77 | 3.91 | 15.24 |
| 24.07 | 3.70 | 4.45 |
| 24.65 | 3.61 | 7.64 |
| 25.76 | 3.46 | 4.91 |
| 26.15 | 3.41 | 13.04 |
| 26.49 | 3.36 | 10.50 |
| 26.91 | 3.31 | 7.68 |
| 28.16 | 3.17 | 7.13 |
| 28.76 | 3.10 | 2.04 |
| 29.76 | 3.00 | 1.15 |
| 33.51 | 2.67 | 1.47 |

Example 8 (Crystal Form H)

Figure 14:
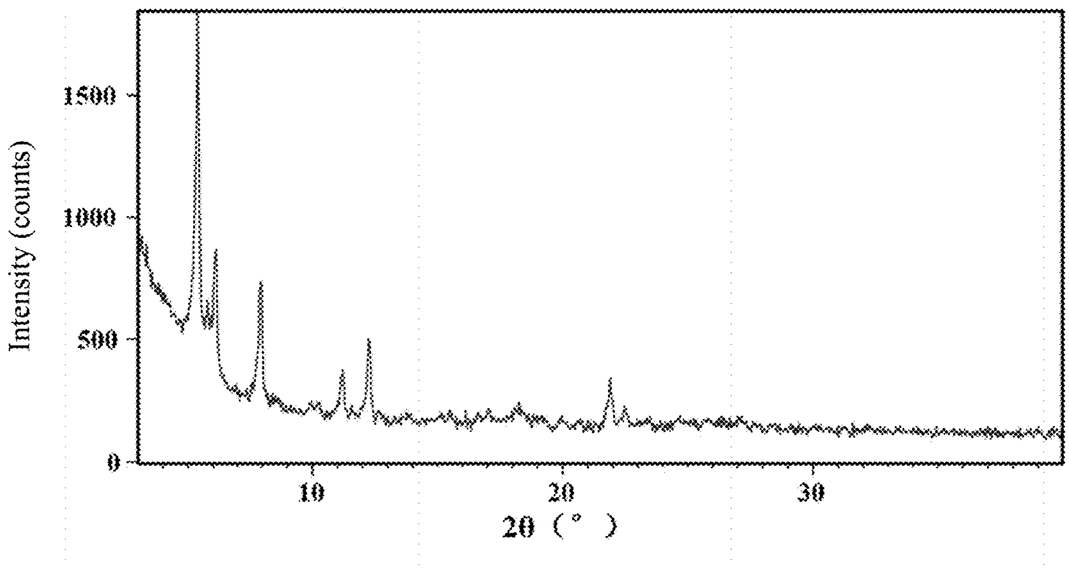
FIG. 14: XRPD pattern of crystal form H.
Figure 15:
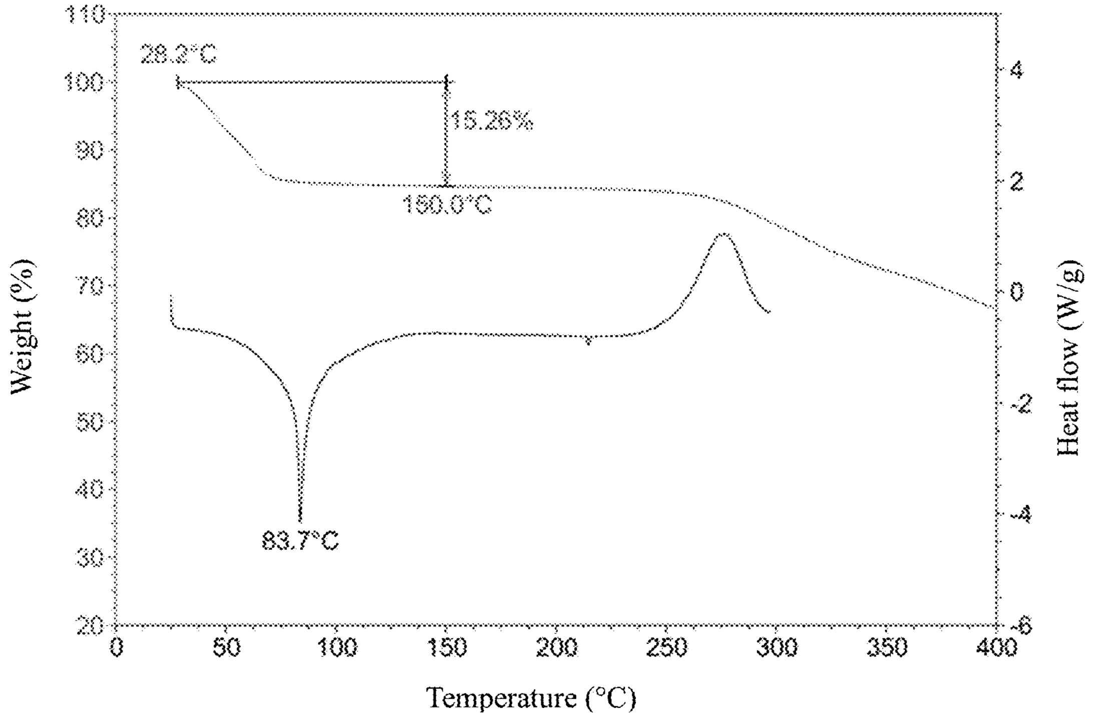
FIG. 15: TGA/DSC pattern of crystal form H.

100 mg of crystal form B of compound 1 was suspended and stirred in 1 mL of water at 50° C. for four days. The X-ray powder diffraction data of the resulting solid are shown in Table 8, and the XRPD pattern thereof is shown in FIG. 14. The TGA/DSC results are shown in FIG. 15. The sample lost 15.3% of its weight when heated from room temperature to 150° C. The DSC results indicate an endothermic peak at 83.7° C. (peak temperature). The results confirm that the resulting solid product is the crystal form H as described in the present disclosure.

TABLE 8

| XRPD data of crystal form H | | |
|---|---|---|
| Diffraction angle (°2θ) | d-Spacing (Å) | Relative intensity (%) |
| 5.41 | 16.35 | 100.00 |
| 6.13 | 14.42 | 35.95 |
| 7.92 | 11.16 | 35.68 |
| 11.19 | 7.90 | 13.58 |
| 12.26 | 7.22 | 22.74 |
| 21.91 | 4.06 | 12.38 |

Example 9 (Crystal Form I)

Figure 16:
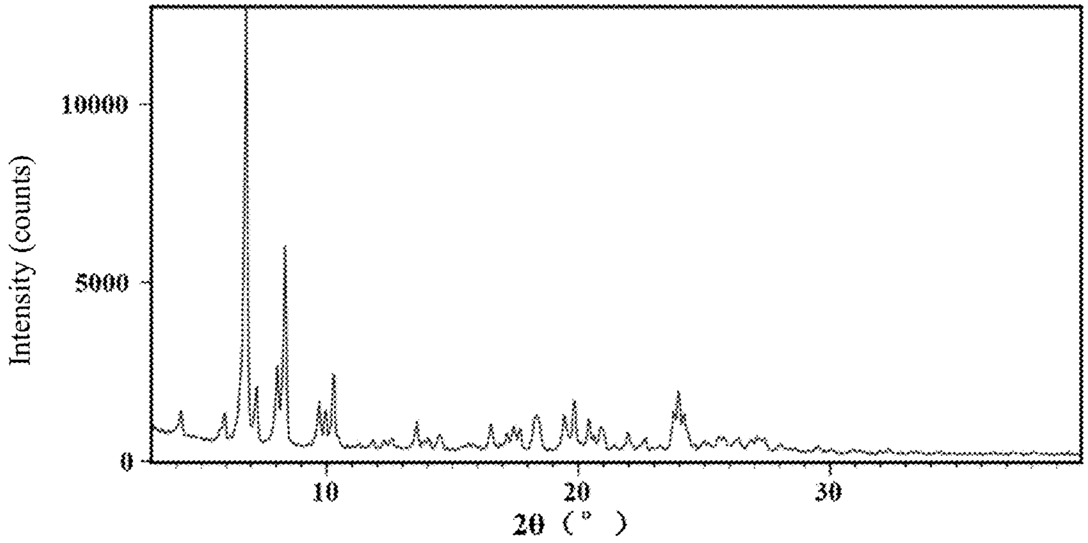
FIG. 16: XRPD pattern of crystal form I.
Figure 17:
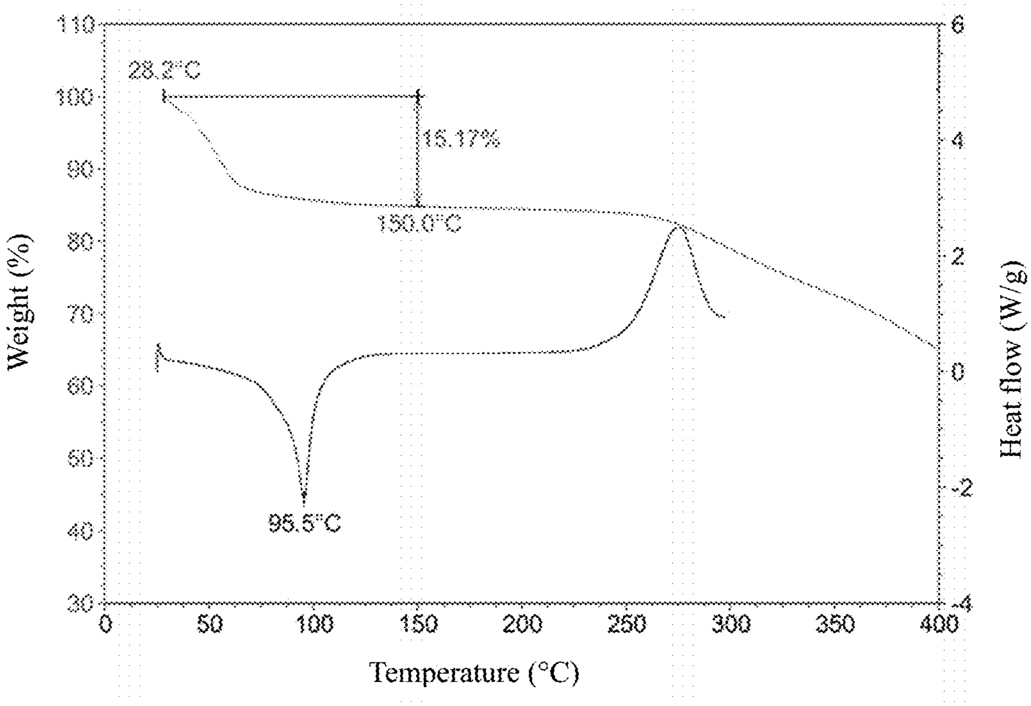
FIG. 17: TGA/DSC pattern of crystal form I.

100 mg of crystal form B of compound 1 was weighed and dissolved in 8 mL of $CHCl_3$/IPA (1:3, v/v). The sample was filtered, then sealed with a sealing film, with several small holes punctured in the sealing film, and left to evaporate naturally in a fume hood. The X-ray powder diffraction data of the resulting solid are shown in Table 9, and the XRPD pattern thereof is shown in FIG. 16. The TGA/DSC results are shown in FIG. 17. The sample lost 15.2% of its weight when heated from room temperature to 150° C. The DSC results indicate an endothermic peak at 95.5° C. (peak temperature). The results confirm that the resulting solid product is the crystal form I as described in the present disclosure.

TABLE 9

| XRPD data of crystal form I | | |
|---|---|---|
| Diffraction angle (°2θ) | d-Spacing (Å) | Relative intensity (%) |
| 4.20 | 21.02 | 9.75 |
| 5.94 | 14.89 | 9.25 |
| 6.80 | 13.00 | 100.00 |
| 7.22 | 12.25 | 15.07 |
| 8.03 | 11.01 | 19.45 |
| 8.35 | 10.59 | 45.93 |
| 9.70 | 9.12 | 11.58 |
| 9.95 | 8.89 | 9.48 |
| 10.28 | 8.61 | 17.97 |
| 11.84 | 7.47 | 2.80 |
| 12.57 | 7.04 | 3.12 |
| 13.57 | 6.52 | 7.25 |
| 14.06 | 6.30 | 3.41 |
| 14.49 | 6.11 | 4.14 |
| 15.52 | 5.71 | 1.51 |
| 16.53 | 5.36 | 6.47 |
| 17.15 | 5.17 | 4.59 |
| 17.42 | 5.09 | 6.40 |
| 17.68 | 5.02 | 5.49 |
| 18.23 | 4.87 | 7.09 |
| 18.43 | 4.82 | 7.63 |
| 19.44 | 4.57 | 8.64 |
| 19.84 | 4.48 | 11.75 |
| 20.41 | 4.35 | 7.85 |
| 20.89 | 4.25 | 5.93 |
| 21.43 | 4.15 | 1.74 |
| 21.97 | 4.05 | 4.73 |
| 22.65 | 3.93 | 3.52 |
| 23.77 | 3.74 | 9.10 |
| 23.98 | 3.71 | 13.88 |
| 24.19 | 3.68 | 8.59 |
| 24.96 | 3.57 | 2.88 |
| 25.56 | 3.49 | 3.91 |
| 26.34 | 3.38 | 3.40 |

TABLE 9-continued

| XRPD data of crystal form I | | |
|---|---|---|
| Diffraction angle (°2θ) | d-Spacing (Å) | Relative intensity (%) |
| 26.81 | 3.33 | 2.93 |
| 27.40 | 3.25 | 3.20 |
| 28.02 | 3.18 | 1.87 |
| 29.50 | 3.03 | 1.31 |
| 31.00 | 2.88 | 0.62 |
| 32.36 | 2.77 | 0.94 |
| 38.09 | 2.36 | 0.37 |

Example 10 (Crystal Form J)

Figure 18:
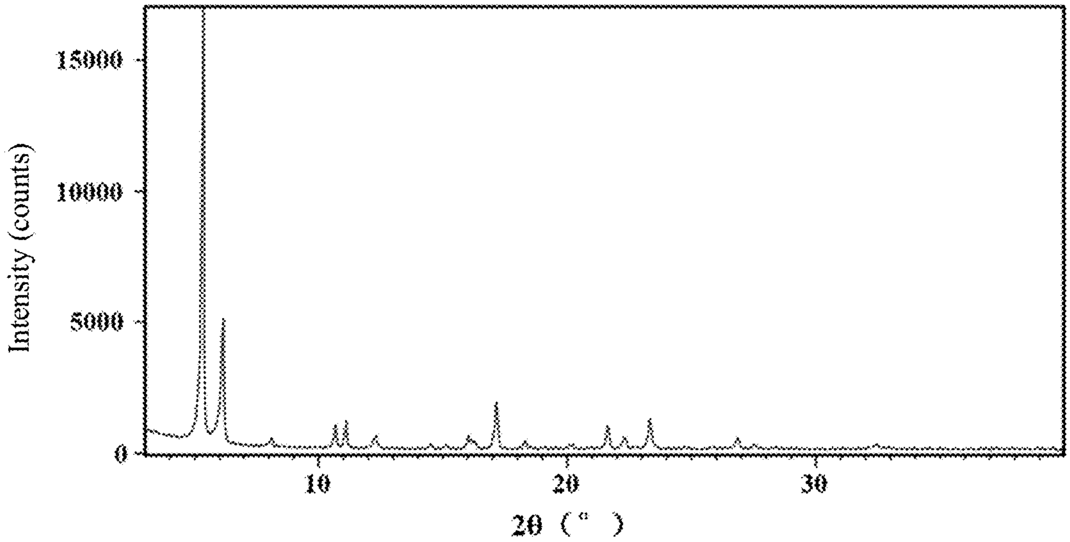
FIG. 18: XRPD pattern of crystal form J.

20 mg of crystal form B of compound 1 was dissolved in 0.2 mL of dimethyl sulfoxide (DMSO). The resulting sample was filtered, and 5 mL of MIBK (4-methyl-2-pentanone) was added dropwise to the bottle with magnetic stirring. The sample was then allowed to evaporate at room temperature with the container open until a solid formed. The X-ray powder diffraction data of the resulting solid are shown in Table 10, and the XRPD pattern thereof is shown in FIG. 18. The results confirm that the resulting solid product is the crystal form J as described in the present disclosure.

TABLE 10

| XRPD data of crystal form J | | |
|---|---|---|
| Diffraction angle (°2θ) | d-Spacing (A) | Relative intensity (%) |
| 5.34 | 16.54 | 100.00 |
| 6.15 | 14.38 | 28.86 |
| 8.1 | 10.91 | 2.02 |
| 10.68 | 8.29 | 5.66 |
| 11.1 | 7.97 | 6.01 |
| 12.29 | 7.20 | 3.00 |
| 14.53 | 6.10 | 1.00 |
| 15.13 | 5.85 | 0.66 |
| 16.02 | 5.53 | 3.11 |
| 17.16 | 5.17 | 10.50 |
| 18.31 | 4.85 | 1.88 |
| 19.07 | 4.65 | 0.42 |
| 20.16 | 4.40 | 0.97 |
| 21.63 | 4.11 | 5.22 |
| 22.32 | 3.98 | 2.70 |
| 23.32 | 3.81 | 6.62 |
| 26.85 | 3.32 | 2.86 |
| 27.55 | 3.24 | 1.10 |
| 32.46 | 2.76 | 0.93 |

Example 11 (Crystal Form K)

Figure 19:
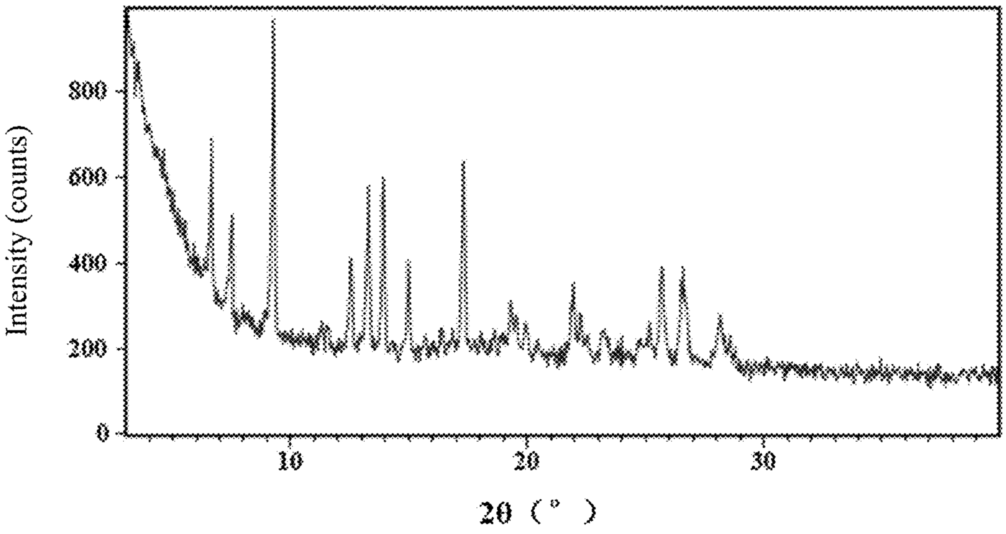
FIG. 19: XRPD pattern of crystal form K.

100 mg of crystal form B of compound 1 was weighed and dissolved in 20 mL of $CHCl_3$/MeOH (1:20, v/v). The sample was filtered and then allowed to evaporate with the container open until a solid formed. The X-ray powder diffraction data of the resulting solid are shown in Table 11, and the XRPD pattern thereof is shown in FIG. 19. The results confirm that the resulting solid product is the crystal form K as described in the present disclosure.

TABLE 11

| XRPD data of crystal form K | | |
|---|---|---|
| Diffraction angle (°2θ) | d-Spacing (Å) | Relative intensity (%) |
| 6.63 | 13.33 | 47.55 |
| 7.49 | 11.81 | 28.07 |
| 9.26 | 9.55 | 100.00 |
| 12.54 | 7.06 | 29.34 |
| 13.28 | 6.67 | 51.57 |
| 13.61 | 6.51 | 0.36 |
| 13.92 | 6.36 | 54.12 |
| 14.97 | 5.92 | 28.88 |
| 17.29 | 5.13 | 61.37 |
| 19.41 | 4.57 | 11.55 |
| 21.93 | 4.05 | 20.82 |
| 23.25 | 3.83 | 8.93 |
| 25.69 | 3.47 | 31.10 |
| 26.56 | 3.36 | 24.04 |
| 28.14 | 3.17 | 13.70 |

Example 12 (Crystal Form L)

Figure 20:
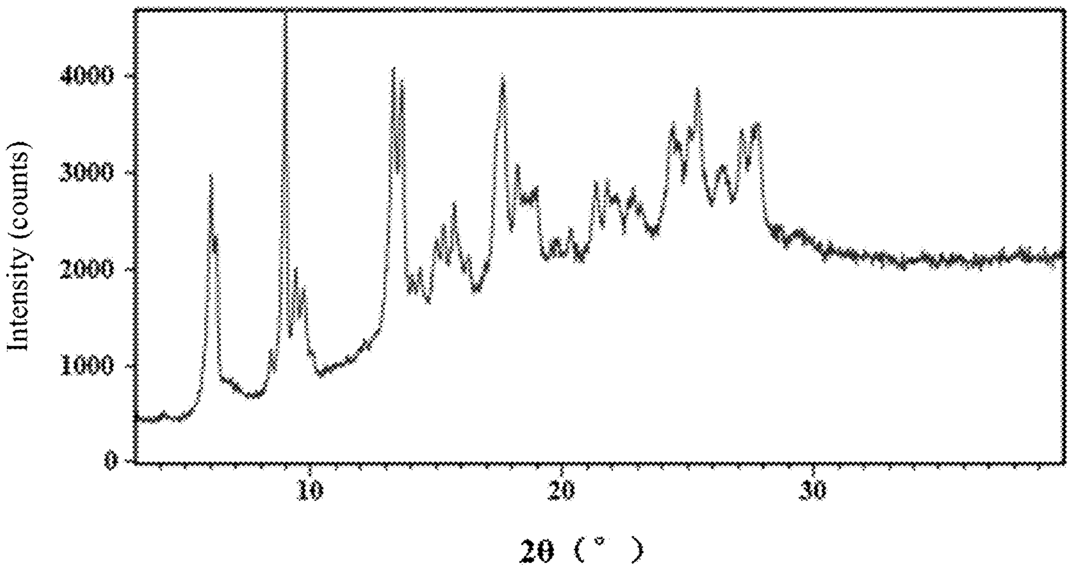
FIG. 20: XRPD pattern of crystal form L.

The crystal form E obtained in Example 5 was purged with nitrogen gas for ten minutes. The X-ray powder diffraction data of the resulting solid are shown in Table 12, and the XRPD pattern thereof is shown in FIG. 20. The results confirm that the resulting solid product is crystal form L as described in the present disclosure.

TABLE 12

| XRPD data of crystal form L | | |
|---|---|---|
| Diffraction angle (°2θ) | d-Spacing (A) | Relative intensity (%) |
| 6.02 | 14.69 | 61.59 |
| 6.25 | 14.15 | 42.99 |
| 8.39 | 10.54 | 9.07 |
| 8.99 | 9.84 | 100.00 |
| 9.38 | 9.43 | 30.03 |
| 9.72 | 9.10 | 22.68 |
| 13.29 | 6.66 | 73.09 |
| 13.62 | 6.50 | 67.03 |
| 14.34 | 6.18 | 17.74 |
| 14.98 | 5.91 | 24.10 |
| 15.29 | 5.79 | 27.64 |
| 15.7 | 5.65 | 32.71 |
| 16.27 | 5.45 | 17.59 |
| 17.36 | 5.11 | 45.43 |
| 17.67 | 5.02 | 58.37 |
| 18.21 | 4.87 | 37.98 |
| 18.95 | 4.68 | 29.36 |
| 20.33 | 4.37 | 17.38 |
| 21.34 | 4.16 | 27.50 |
| 21.78 | 4.08 | 27.23 |
| 22.75 | 3.91 | 20.74 |
| 24.38 | 3.65 | 35.96 |
| 25.45 | 3.50 | 44.63 |
| 26.44 | 3.37 | 23.19 |
| 27.14 | 3.29 | 31.70 |
| 27.82 | 3.21 | 31.52 |

Example 13 (Crystal Form M)

Figure 21:
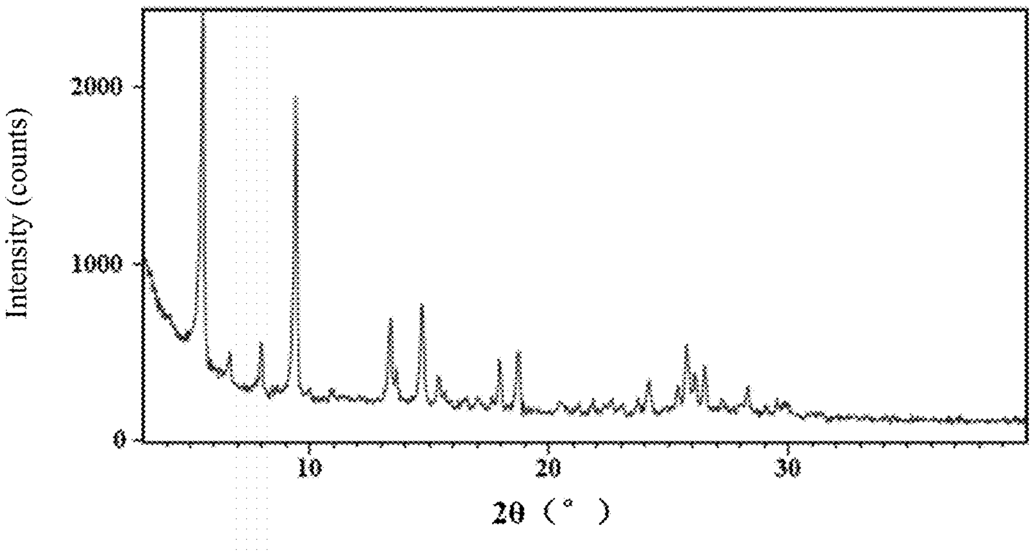
FIG. 21: XRPD pattern of crystal form M.
Figure 22:
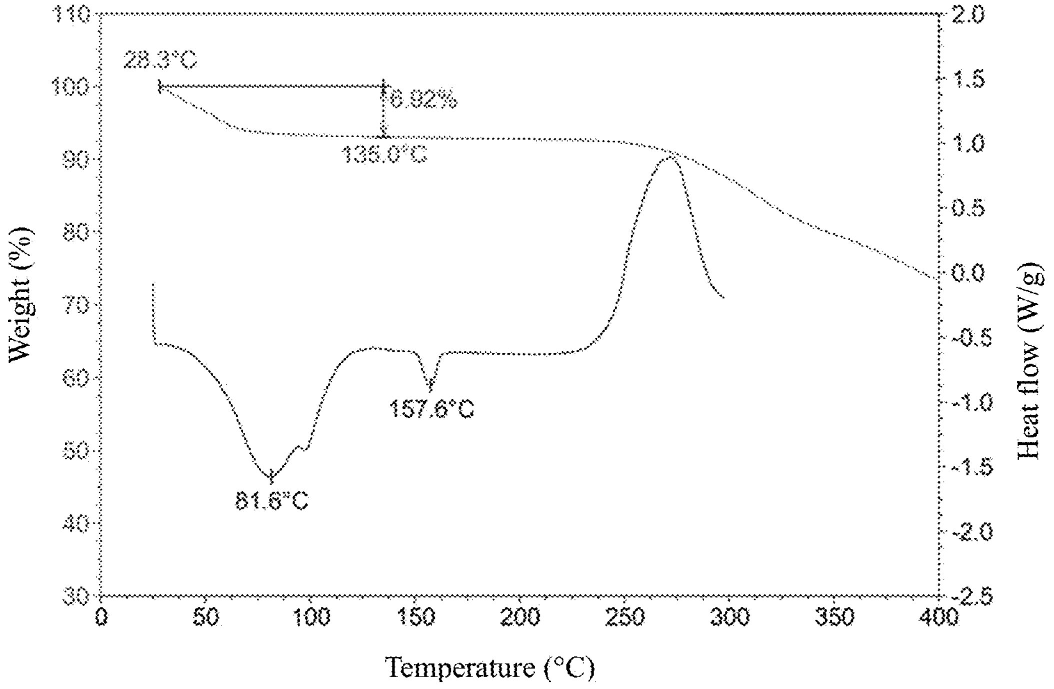
FIG. 22: TGA/DSC pattern of crystal form M.

100 mg of crystal form B of compound 1 was suspended and stirred in 1 mL of Acetone/$H_2O$ (605:395, v/v) at room temperature for six days. The X-ray powder diffraction data of the resulting solid are shown in Table 13, and the XRPD pattern thereof is shown in FIG. 21. The TGA/DSC results are shown in FIG. 22. The sample lost 6.9% of its weight when heated from room temperature to 135° C. Two endothermic peaks were observed at 81.6° C. (onset temperature)

and 157.6° C. (onset temperature). The results confirm that the resulting solid product is the crystal form M as described in the present disclosure.

TABLE 13

XRPD data of crystal form M

| Diffraction angle (°2θ) | d-Spacing (Å) | Relative intensity (%) |
|---|---|---|
| 5.52 | 16.00 | 100.00 |
| 6.62 | 13.36 | 7.21 |
| 7.96 | 11.10 | 13.70 |
| 9.41 | 9.40 | 87.09 |
| 13.36 | 6.63 | 24.72 |
| 14.68 | 6.04 | 29.13 |
| 15.39 | 5.76 | 8.21 |
| 17.93 | 4.95 | 14.08 |
| 18.70 | 4.75 | 16.58 |
| 20.51 | 4.33 | 2.57 |
| 24.17 | 3.68 | 9.22 |
| 25.75 | 3.46 | 20.55 |
| 26.11 | 3.41 | 11.39 |
| 26.50 | 3.36 | 13.80 |
| 28.31 | 3.15 | 7.97 |
| 29.67 | 3.01 | 2.84 |

Crystal Form Transformation Relationship Examples

Example 1: Suspension Competition Test Between Crystal Forms B and C

Figure 23:
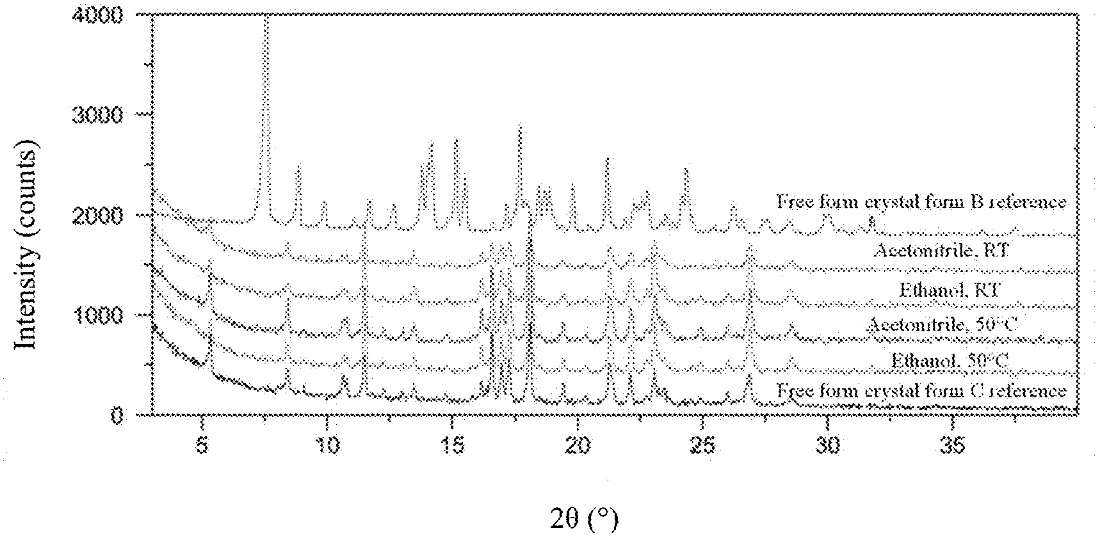
FIG. 23: Comparative XRPD patterns of the suspension competition between crystal forms B and C.

A suspension competition test was set up between the two crystal forms in acetonitrile and ethanol at room temperature and 50° C. The results of the test are summarized in Table 14. The specific steps are as follows:

1) Saturated solutions of crystal form B in acetonitrile and ethanol were prepared at room temperature and 50° C., respectively, and then filtered;

2) approximately 5 mg of crystal forms B and C were respectively added to 0.5 mL of the saturated solutions of crystal form B in ethanol and acetonitrile; the resulting suspensions were respectively suspended and stirred at room temperature and 50° C. for two days;

3) the resulting solids were isolated and analyzed using XRPD, and the results are shown in FIG. 23.

Example 2: Suspension Competition Test Among Crystal Forms C/A/G/H/I/M/E

Figure 24:
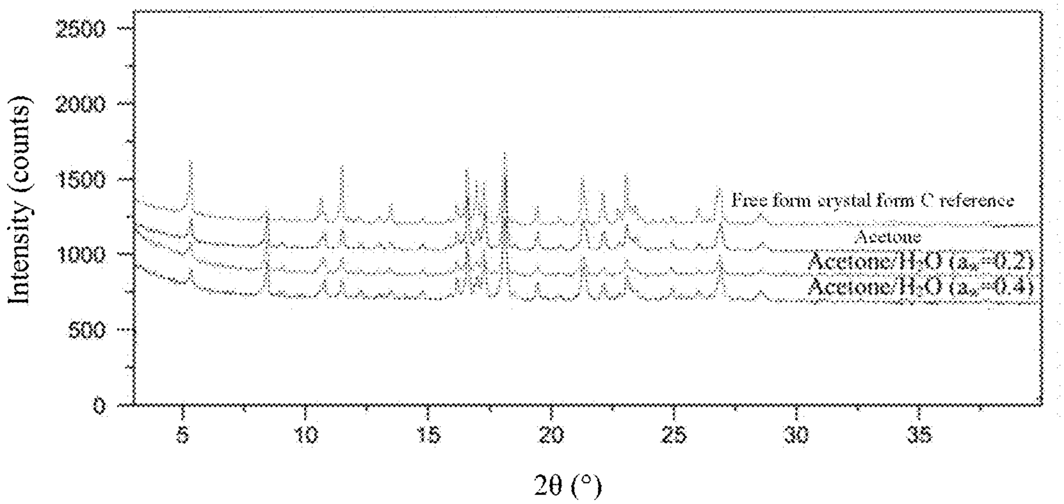
FIG. 24: Comparative XRPD patterns of the suspension competition among the mixtures of crystal forms C/A/G/H/I/M/E.

A suspension competition test was performed at room temperature among crystal forms C/A/G/H/I/M/E in acetone or in Acetone/$H_2O$ mixtures with different volume ratios (986/14, v/v and 950/50, v/v). The results are summarized in Table 14. The specific steps are as follows:

1) Saturated solutions of crystal forms C/A/G/H/I/M/E were prepared at room temperature in the respective solvent systems and filtered;

2) approximately 5 mg of crystal forms C/A/G/H/I/M/E were added to 0.5 mL of the respective saturated solutions, and the resulting suspensions were suspended and stirred overnight at room temperature;

3) the resulting solids were isolated and analyzed using XRPD, and the results are shown in FIG. 24.

TABLE 14

Summary of suspension competition tests for various crystal forms

| Initial crystal form | Solvent | Temperature | Resulting crystal form |
|---|---|---|---|
| Crystal form B/C | Acetonitrile | Room temperature | Crystal form C |
| | Ethanol | Room temperature | |
| | Acetonitrile | 50° C. | |
| | Ethanol | 50° C. | |
| Crystal forms C/A/G/H/I/M/E | Acetone | Room temperature | |
| | Acetone/water (986/14) | | |
| | Acetone/water (950/50) | | |

Conclusion: The XRPD comparison results shown in FIG. 23 and FIG. 24 indicate that the solid samples obtained from each system were consistently crystal form C, suggesting that crystal form C is the more stable form.

Evaluation of the Physicochemical Stability of Crystal Form C

Example 1

Figure 25:
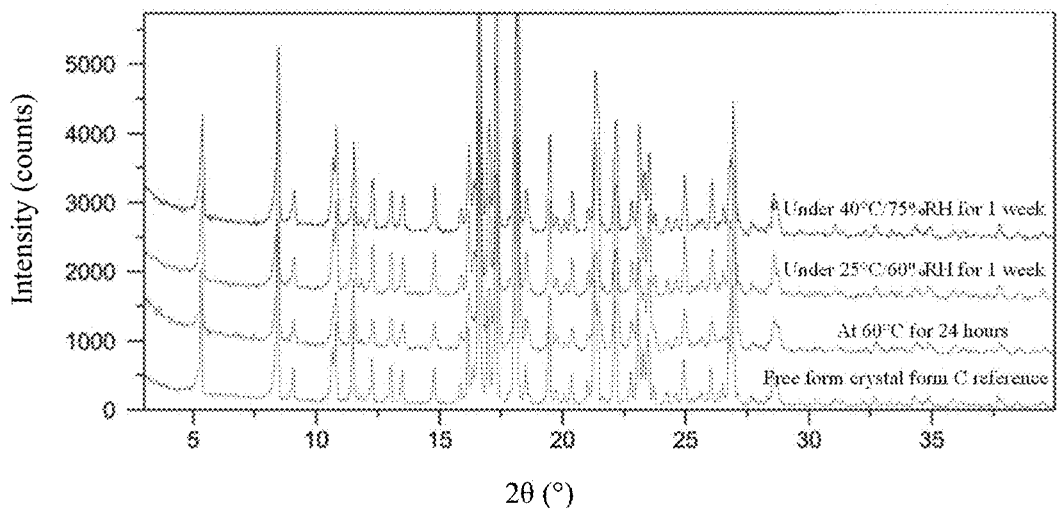
FIG. 25: Comparative XRPD patterns from the stability test of crystal form C.

To assess the physicochemical stability of crystal form C, approximately 20 mg of the crystal form C of compound 1 was weighed and placed in a sealed setting at 60° C. for one day, and in an open setting (sealed with a sealing film, with several small holes punctured in the sealing film) at 25° C./60% RH or 40° C./75% RH for one week, respectively. The solid samples after being placed under different conditions were respectively tested for purity by UPLC to evaluate chemical stability, and the crystal form was tested by XRPD to evaluate physical stability. The evaluation results, summarized in Table 15, indicate that crystal form C did not undergo any crystal transformation under all three test conditions, as confirmed by the XRPD data shown in FIG. 25. Additionally, no significant degradation was observed after one day at 60° C. or one week at 25° C./60% RH and 40° C./75% RH (details of purity changes are provided in Table 16).

TABLE 15

Summary of physicochemical stability evaluation results for crystal form C

| | | | Stability result | | |
|---|---|---|---|---|---|
| Raw material | Condition | Time | Initial purity (area %) | Stability sample purity (area %) | Crystal form change |
| Crystal form C of compound 1 | 60° C. | 24 hours | 99.31 | 99.29 | No change |
| | 25° C./ 60% RH | 1 week | | 99.29 | |
| | 40° C./ 75% RH | | | 99.29 | |

TABLE 16

Summary of impurities in samples of crystal form C for stability testing

| | RRT | | | | | |
|---|---|---|---|---|---|---|
| Sample | 0.63 | 0.67 | 0.95 | 1.00 | 1.03 | 1.08 |
| Initial sample | 0.18% | 0.18% | 0.08% | 99.31% | 0.10% | 0.15% |
| 60° C. | 0.18% | 0.18% | 0.08% | 99.29% | 0.12% | 0.15% |

TABLE 16-continued

| Summary of impurities in samples of crystal form C for stability testing | | | | | | |
|---|---|---|---|---|---|---|
| | RRT | | | | | |
| Sample | 0.63 | 0.67 | 0.95 | 1.00 | 1.03 | 1.08 |
| 25° C./60% RH | 0.18% | 0.18% | 0.08% | 99.29% | 0.12% | 0.15% |
| 40° C./75% RH | 0.18% | 0.18% | 0.08% | 99.29% | 0.12% | 0.15% |

Conclusion: The results indicate that crystal form C exhibits good physical and chemical stability after one day at 60° C. and one week at 25° C./60% RH and 40° C./75% RH.

Effect Example 1: Comparison of Absorption in Rats After Administration of Different Crystal Forms SD rats were intragastrically administered samples of different crystal forms. Blood samples (0.4 mL) were respectively collected from the venous plexus of the rat's fundus oculi at various time points: before administration and at 5, 15, 30, 60, 90, 120, 240, 360, 480, 600, and 1440 minutes after administration. The blood samples were centrifuged at 8000 rpm for 5 minutes to separate the upper plasma. 50 μL of plasma sample was added with 300 μL of acetonitrile containing an internal standard (Propranolol, 25 ng/mL) to precipitate proteins. The mixture was vortexed for 10 minutes, and centrifuged at 6000 g and 4° C. for 20 minutes. The supernatant (20 μL) was taken and diluted with 80 μL of ultrapure water. After centrifugation, 80 μL of the supernatant was taken for injection into a 96-well plate. The plasma drug concentration was determined using LC/MS/MS, and the corresponding pharmacokinetic parameters were calculated, as shown in Table 17.

TABLE 17

| Pharmacokinetic parameters after intragastric administration of different crystal forms | | | | | | |
|---|---|---|---|---|---|---|
| Parameter | | Amorphous form | Crystal form A | Crystal form B | Crystal form C | Crystal form M |
| Dosage | mg/kg | 8.00 | 8.00 | 8.00 | 8.00 | 8.00 |
| Cmax | ng/mL | 800 | 753 | 599 | 1165 | 489 |
| Tmax | h | 6.00 | 2.00 | 6.00 | 2.00 | 2.00 |
| AUClast | (h)*(ng/mL) | 6536 | 4789 | 5904 | 6863 | 2870 |
| AUCextra | (h)*(ng/mL) | 0.758 | 0.288 | 1.01 | 0.451 | 0.169 |
| AUCtot | (h)*(ng/mL) | 6586 | 4802 | 5965 | 6894 | 2875 |
| $t_{1/2}$ | h | 3.03 | 2.74 | 3.34 | 3.04 | 2.55 |
| MRT | h | 6.52 | 4.74 | 6.07 | 4.63 | 4.59 |

Conclusion: In this experiment, amorphous form, crystal form A, crystal form B, crystal form C, and crystal form M were each administered to rats by intragastric administration at a dose of 8 mg/kg.
The results indicate that crystal form C exhibits the most favorable pharmacokinetic parameters.

Effect Example 2: EGFR/ErbB2 Enzymatic Assay

First, a 1× reaction buffer required for the kinase was prepared by diluting the 5× Enzymatic Buffer (HEPES 20 mM, pH 7.0, $NaN_3$ 0.1%, BSA 0.05%, sodium orthovanadate 0.5 mM) from the HTRF kinEASE-TK kit with deionized water to one-fold. At the same time, 50 nM Supplement Enzymatic Buffer (SEB reagent), 1 mM $MnCl_2$, 5 mM $MgCl_2$, and 1 mM DTT were added. Next, a 5× compound solution was prepared. A 10 mM stock solution of the test compound (crystal form C prepared in Example 3) was serially diluted in DMSO in a 96-well compound plate to obtain a compound solution with an initial concentration of 100×. This initial concentration was then used as the first concentration, and further diluted with DMSO in a 3-fold serial dilution to dilute a total of 10 concentrations. Subsequently, 1 μL of the serially diluted solution was added to 19 μL of 1× reaction buffer to prepare the 5× compound solution for later use. Then, 2 μL of the 5× compound solution was transferred from the 96-well plate into a 384-well plate. In the no-compound control wells, 2 μL of a mixture of 1 μL DMSO and 19 μL 1× reaction buffer was added. In the blank control wells, 2 μL of 250 mM EDTA was added. In the third step, the enzyme reaction stage, the kinase, substrate (TK Substrate-biotin), and ATP were prepared into a 2.5× enzyme/substrate mixture and a 2.5× ATP solution using the 1× reaction buffer. The final concentration of ErbB2 kinase (Sigma E2645-500UN) was 0.06 ng/μL, with an ATP final concentration of 4 μM. The final concentration of EGFR kinase (Carna 08-016) was 0.06 units/μL, with an ATP final concentration of 1.65 μM. 4 μL of the 2.5× enzyme/substrate mixture was added to the 384-well plate, followed by incubation at room temperature for 5 minutes. Then, 4 μL of the 2.5× ATP solution was added to each well, and the reaction was carried out at room temperature for 30 minutes. In the fourth step, the reaction termination stage, a 2× mixture of TK Antibody-Eu(K) and Sa-XL665 was prepared using HTRF Detection Buffer, with 5 μL of TK Antibody-Eu(K) added per well. After the enzyme reaction was carried out for 30 minutes, 10 μL of this mixture was added to the 384-well plate. The reaction was carried out at room temperature for 1 hour. Data were measured on EnVision™, with a 337 nm laser used as the excitation light. The RFU was measured at 665 nm and 620 nm, and RFU 665 nM/RFU 620 nM×10000 was used as the final data for analysis.

| | Kinase IC50 (nM) | |
|---|---|---|
| Compound | HER2 | EGFR |
| Crystal form C | 0.26 | 1.45 |

Although the specific embodiments of the present disclosure have been described above, it should be understood by those skilled in the art that these are merely illustrative. The scope of protection of the present disclosure is defined by the appended claims. Various changes or modifications may be made to these embodiments by those skilled in the art without departing from the principles and spirit of the present disclosure, and all such changes and modifications fall within the scope of protection of the present disclosure.

What is claimed is:

1. A crystal form C of compound 1, wherein the crystal form C has an X-ray powder diffraction pattern expressed in 2θ angles comprising diffraction peaks at positions as follows: 5.32±0.2°, 8.42±0.2°, 10.62±0.2°, 11.48±0.2°, 13.46±0.2°, 16.14±0.2°, 16.57±0.2°, 16.96±0.2°, 17.26±0.2°, and 18.11±0.2° using Cu-Kα radiation;

1

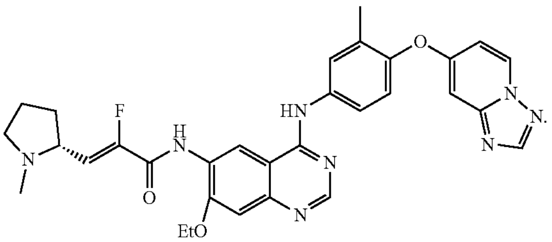

2. The crystal form C according to claim 1, wherein the crystal form C satisfies one or more conditions as follows:

(1) the X-ray powder diffraction pattern of the crystal form C expressed in 2θ angles further comprises diffraction peaks at one or more positions as follows: 19.42±0.2°, 21.26±0.2°, 22.11±0.2°, 22.73±0.2°, 23.05±0.2°, 23.45±0.2°, 25.98±0.2°, 26.71±0.2°, and 26.89±0.2°;

(2) the crystal form C has a differential scanning calorimetry pattern comprising an endothermic peak at 213.3° C.; and (3) the crystal form C has a thermogravimetric analysis pattern showing a weight loss of 2.1% when heated to 200° C. and an additional weight loss of 1.5% when further heated to 230° C.

3. The crystal form C according to claim 2, wherein the crystal form C satisfies one or more conditions as follows:

(1) the X-ray powder diffraction pattern of the crystal form C expressed in 2θ angles comprises diffraction peaks as shown in the table below:

| Diffraction angle (°2θ) | Relative intensity (%) |
|---|---|
| 5.32 | 74.21 |
| 8.42 | 16.85 |
| 10.62 | 33.15 |
| 11.48 | 76.93 |
| 12.23 | 7.17 |
| 13.00 | 8.22 |
| 13.46 | 26.98 |
| 14.76 | 8.36 |
| 16.14 | 28.59 |
| 16.57 | 78.16 |
| 16.96 | 58.96 |
| 17.26 | 55.51 |
| 18.11 | 100.00 |
| 19.42 | 24.10 |
| 20.33 | 10.44 |
| 21.26 | 65.07 |
| 22.11 | 44.06 |
| 22.73 | 22.24 |
| 23.05 | 68.68 |
| 23.45 | 26.23 |
| 24.89 | 10.74 |
| 25.98 | 23.94 |
| 26.71 | 38.70 |
| 26.89 | 55.25 |
| 28.50 | 18.99 |

-continued

| Diffraction angle (°2θ) | Relative intensity (%) |
|---|---|
| 31.74 | 7.39 |
| 34.46 | 1.90 |
| 35.94 | 1.47 |
| 37.67 | 3.97; |

(2) the differential scanning calorimetry pattern of the crystal form C comprises an endothermic peak at 213.3° C., with a heat of fusion of 95.16 J/g; and (3) the thermogravimetric analysis pattern of the crystal form C is basically as shown in FIG. 6.

4. The crystal form C according to claim 3, wherein the crystal form C satisfies one or two conditions as follows:

(1) the X-ray powder diffraction pattern of the crystal form C expressed in 2θ angles is basically as shown in FIG. 5; and (2) the differential scanning calorimetry pattern of the crystal form C is basically as shown in FIG. 6.

5. A preparation method for the crystal form C according to claim 1, wherein the preparation method follows scheme 1 or scheme 2, wherein the scheme 1 comprises the following step: obtaining the crystal form C of the compound 1 by performing a crystal transformation on a suspension of compound 1 in a solvent;

1

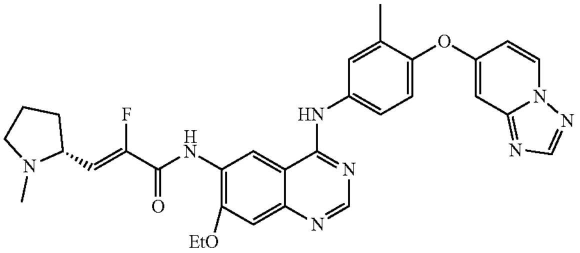

the compound 1 exists in crystal forms B, A, G, H, I, M, or E; the crystal form B has an X-ray powder diffraction pattern expressed in 2θ angles comprising diffraction peaks at positions as follows: 7.53±0.2°, 8.83±0.2°, 12.72±0.2°, 13.98±0.2°, 14.20±0.2°, 15.05±0.2°, 15.44±0.2°, 17.68±0.2°, 18.13±0.2°, 18.38±0.2°, 18.86±0.2°, 21.24±0.2°, 22.44±0.2°, and 24.54±0.2° using Cu-Kα radiation; the crystal form A has an X-ray powder diffraction pattern expressed in 2θ angles comprising diffraction peaks at positions as follows: 5.97±0.2°, 12.27±0.2°, 13.30±0.2°, 14.31±0.2°, 16.08±0.2°, 16.60±0.2°, 17.93±0.2°, and 20.24±0.2° using Cu-Kα radiation; the crystal form G has an X-ray powder diffraction pattern expressed in 2θ angles comprising diffraction peaks at positions as follows: 6.41±0.2°, 6.88±0.2°, 8.75±0.2°, 12.82±0.2°, 13.38±0.2°, 13.73±0.2°, 16.74±0.2°, 17.64±0.2°, 19.24±0.2°, 21.68±0.2°, 22.77±0.2°, 26.14±0.2°, and 26.49±0.2° using Cu-Kα radiation; the crystal form H has an X-ray powder diffraction pattern expressed in 2θ angles comprising diffraction peaks at positions as follows: 5.41±0.2°, 6.13±0.2°, 7.92±0.2°, 11.19±0.2°, 12.26±0.2°, and 21.91±0.2° using Cu-Kα radiation; the crystal form I has an X-ray powder diffraction pattern expressed in 2θ angles comprising diffraction peaks at positions as follows: 6.80±0.2°, 7.22±0.2°, 8.03±0.2°, 8.35±0.2°, 9.70±0.2°, 10.28±0.2°, and 19.84±0.2° using Cu-Kα radiation; the crystal form M has an X-ray powder diffraction pattern expressed in 2θ angles comprising diffraction peaks at positions as follows: 5.52±0.2°, 7.96±0.2°, 9.41±0.2°, 13.36±0.2°, 14.68±0.2°, 17.93±0.2°, 18.70±0.2°, 25.75±0.2°, 26.11±0.2°, and 26.50±0.2° using Cu-Kα radiation; the crystal form E has an X-ray powder diffraction pattern expressed in 2θ angles comprising diffraction peaks at positions as follows: 6.07±0.2°, 8.97±0.2°, 9.32±0.2°, 9.87±0.2°, 13.05±0.2°, 13.27±0.2°, 14.09±0.2°, 15.78±0.2°, 16.98±0.2°, 18.27±0.2°, 18.47±0.2°, 21.26±0.2°, and 22.41±0.2° using Cu-Kα radiation;

when the compound 1 exists in crystal forms A, G, H, I, M, or E, the solvent is acetone or acetone/water;

when the compound 1 exists in crystal form B, the solvent is acetonitrile or ethanol;

the scheme 2 comprises the following step: obtaining the crystal form C of the compound 1 by performing a crystallization on compound 1 in a solvent; the solvent is an alcohol solvent.

6. The preparation method for crystal form C according to claim 5, wherein in the scheme 1, the preparation method satisfies one or more conditions as follows:

(1) when the solvent is acetone/water, the volume ratio of acetone to water is between 986:14 and 950:50;

(2) when the compound 1 exists in one of crystal forms A, G, H, I, M, and E, the crystal transformation is performed at a temperature of 20° C. to 30° C.; and (3) when the compound 1 exists in crystal form B, the crystal transformation is performed at a temperature of 20° C. to 50° C.

7. The preparation method for crystal form C according to claim 5, wherein in the scheme 2, the preparation method satisfies one or more conditions as follows:

(1) the mass-to-volume ratio of the compound 1 to the solvent is 100 mg: 2 mL;

(2) the crystallization is performed at a temperature of 50° C. to 60° C.; and (3) the crystallization is performed for a duration of 24 hours.

8. A pharmaceutical composition comprising the crystal form C according to claim 1 and a pharmaceutical excipient.

9. A method for treating diseases in a subject in need thereof, wherein comprising administering a therapeutically effective amount of the crystal form C according to claim 1, wherein the diseases are cancer or diseases treated by inhibiting EGFR or ErbB2 receptor tyrosine kinases.

10. The method according to claim 9, wherein the diseases are cancer or diseases treated by selectively inhibiting the ErbB2 receptor tyrosine kinase;

or, the cancer and diseases are breast cancer, gastric cancer, ovarian cancer, or lung cancer.

11. A method for treating diseases in a subject in need thereof, wherein comprising administering a therapeutically effective amount of the pharmaceutical composition according to claim 8, the diseases are cancer or diseases treated by inhibiting EGFR or ErbB2 receptor tyrosine kinases.

12. The method according to claim 11, wherein the diseases are cancer or diseases treated by selectively inhibiting the ErbB2 receptor tyrosine kinase;

or, the cancer and diseases are breast cancer, gastric cancer, ovarian cancer, or lung cancer.

13. A method for inhibiting an EGFR or ErbB2 receptor tyrosine kinase in a subject in need thereof, comprising administering a therapeutically amount of the crystal form C according to claim 1.

14. The method according to claim 11, wherein the EGFR or ErbB2 receptor tyrosine kinase inhibitor is a selective ErbB2 receptor tyrosine kinase inhibitor.

15. A method for inhibiting an EGFR or ErbB2 receptor tyrosine kinase in a subject in need thereof, comprising administering a therapeutically amount of the pharmaceutical composition according to claim 8.

16. The method according to claim 15, wherein the EGFR or ErbB2 receptor tyrosine kinase inhibitor is a selective ErbB2 receptor tyrosine kinase inhibitor.

17. The crystal form C according to claim 2, wherein the X-ray powder diffraction pattern of the crystal form C expressed in 2θ angles comprises diffraction peaks at one or more positions as follows: 12.23±0.2°, 13.00±0.2°, 14.76±0.2°, 20.33±0.2°, 24.89±0.2°, 28.50±0.2°, 31.74±0.2°, 34.46±0.2°, 35.94±0.2°, and 37.67±0.2°.

18. The preparation method for crystal form C according to claim 5, wherein in the scheme 2, the solvent is ethanol or isopropanol.

19. The preparation method for crystal form C according to claim 7, wherein in the scheme 2, the crystallization is performed at a temperature of 55° C.

* * * * *